United States Patent [19]

Wenderoth et al.

[11] Patent Number: 5,145,980
[45] Date of Patent: Sep. 8, 1992

[54] OXIME ETHERS, AND FUNGICIDES CONTAINING SAME

[75] Inventors: Bernd Wenderoth, Lampertheim; Hubert Sauter; Horst Wingert, both of Mannheim; Michael Hepp, Ladenburg; Siegbert Brand, Weinheim; Thomas Kuekenhoehner, Frankenthal; Franz Roehl; Eberhard Ammermann, both of Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 509,588

[22] Filed: Apr. 16, 1990

[30] Foreign Application Priority Data

May 27, 1989 [DE] Fed. Rep. of Germany ....... 3917352

[51] Int. Cl.$^5$ ............................................. C07C 229/36
[52] U.S. Cl. ..................................................... 560/35
[58] Field of Search .................. 560/35; 514/530, 531, 514/539

[56] References Cited

U.S. PATENT DOCUMENTS

| | | | |
|---|---|---|---|
| 4,709,078 | 11/1987 | Schirmer et al. | 560/60 |
| 4,723,034 | 2/1988 | Schirmer et al. | 560/60 |
| 4,782,177 | 11/1988 | Schirmer et al. | 560/60 |
| 4,822,908 | 4/1989 | Karbach et al. | 560/60 |
| 4,829,085 | 5/1989 | Wenderoth et al. | 514/522 |

FOREIGN PATENT DOCUMENTS

| | | |
|---|---|---|
| 0253213 | 1/1988 | European Pat. Off. |
| 0254426 | 1/1988 | European Pat. Off. |

*Primary Examiner*—Jose G. Dees
*Assistant Examiner*—B. Frazier
*Attorney, Agent, or Firm*—Oblon, Spivak, McClelland, Maier & Neustadt

[57] ABSTRACT

Oxime ethers of the formula

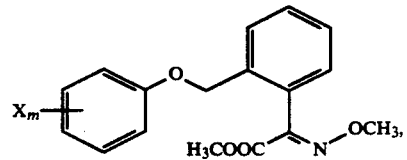

I where X (m=1 to 5) denotes identical or different substituents selected from halogen, cyano, nitro, alkyl, cycloalkyl, alkenyl, alkoxy, haloalkyl, haloalkoxy, substituted or unsubstituted phenyl, substituted or unsubstituted phenoxy, substituted or unsubstituted benzyl or a substituted or unsubstituted fused aromatic ring, with the exception of several known compounds, and fungicides containing these novel compounds.

7 Claims, No Drawings

OXIME ETHERS, AND FUNGICIDES CONTAINING SAME

The present invention relates to novel oxime ethers, their preparation, fungicides containing same, and their use as fungicides.

It is known to use oxime ether derivatives, such as, for example, methyl 2-phenoxymethylphenylglyoxylate O-methyl oxime, as fungicides (EP 253,213 and EP 254,426).

We have found that novel oxime ethers of the general formula I

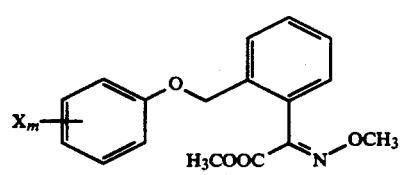

in which X (m=1 to 5) is identical or different substituents halogen, cyano, nitro, $C_1$–$C_{15}$-alkyl, $C_3$–$C_6$-cycloalkyl, $C_3$–$C_6$-cycloalkenyl, $C_1$–$C_4$-alkoxy, $C_1$–$C_2$-haloalkyl, $C_1$–$C_2$-haloalkoxy, substituted or unsubstituted phenyl, substituted or unsubstituted phenoxy, substituted or unsubstituted benzyl or a substituted or unsubstituted fused aromatic ring or a fused cyclohexone ring, with the exception of compounds in which $X_m$ is 2-fluoro, 2-chloro, 3-chloro, 4-chloro, 2,4-dichloro, 2-methyl-4-chloro, 2-methyl, 4-methyl, 4-tert.-butyl, 2-methoxy, 4-methoxy, 2-trifluoromethyl or 4-nitro, have a superior fungicidal action than the abovementioned known compounds.

The radicals mentioned in the general formula I may have, for example, the following meaning: X (m=1 to 5, in particular 1 to 3) can be, for example: halogen (for example fluorine, chlorine, bromine or iodine), cyano, nitro, $C_1$–$C_{15}$-alkyl ($C_1$–$C_{10}$-alkyl) (for example methyl, ethyl, n- or i-propyl; n-, i-, s- or t-butyl; pentyl, hexyl, heptyl, octyl, nonyl or decyl), $C_3$–$C_6$-cycloalkyl (for example cyclopropyl, cyclopentyl or cyclohexyl), $C_3$–$C_6$-alkenyl (for example 1-propenyl or 2-propenyl), $C_1$–$C_4$-alkoxy (for example methoxy, ethoxy, n-propoxy, i-propoxy, n-butoxy or t-butoxy), $C_1$–$C_2$-haloalkyl (for example difluoromethyl, trifluoromethyl, chloromethyl, dichloromethyl, trichloromethyl or pentafluoroethyl), $C_1$–$C_2$-haloalkoxy (for example trifluoromethoxy, difluoroethoxy, tetrafluoroethoxy or pentafluoroethoxy), substituted or unsubstituted phenyl (for example phenyl, $C_1$–$C_4$-alkylphenyl or halophenyl), substituted or unsubstituted phenoxy (for example phenoxy, $C_1$–$C_4$-alkylphenoxy or halophenoxy), substituted or unsubstituted benzyl (for example benzyl or halobenzyl) or a substituted or unsubstituted fused aromatic ring, which results, for example, in 1-naphthyl or 2-naphthyl derivatives or a fused cyclohexane ring instead of phenyl derivatives.

Due to the C=N double bond, the novel compounds of the general formula I can exist in the form of either E or Z isomers, which can be separated in the customary manner. The individual isomeric compounds and their mixtures are covered by the invention and can be used as fungicides.

The novel compounds of the general formula I can be prepared, for example, in accordance with scheme 1:

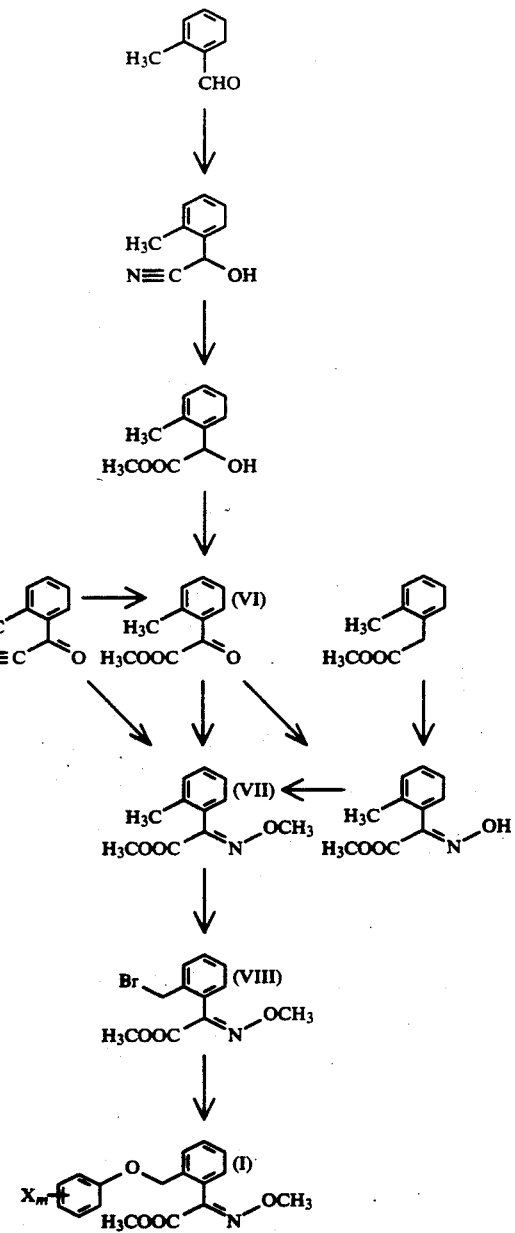

Scheme 1:

The known methyl 2-methylphenylglyoxylate VI (cf., for example, J.M. Photis, Tetrahedron Lett. 1980, 3539) can be prepared, for example, by converting 2-methylbenzaldehyde by known processes using potassium cyanide or sodium cyanide into 2-methylbenzaldehydecyanohydrin, from which methyl 2-methylmandelate can be prepared in the presence of methanol and a protic acid, such as, for example, hydrochloric acid (cf., for example, U.S. Pat. No. 2,892,847). Reaction with a suitable oxidant, such as, for example, sodium hypochlorite, if necessary in the presence of an appropriate catalyst, such as tetrabutylammonium bisulfate, tetrabutylammonium bromide (cf., for example, EP 140,454) or tetramethylpiperidine N-oxide, gives the methyl ester VI, which is also readily accessible from 2-methylbenzoyl nitrile by reaction with sulfuric acid/ methanol in the presence of sodium bromide (cf., for example, J.M. Photis, Tetrahedron Lett. 1980, 3539).

Methyl 2-methylphenylglyoxylate O-methyl oxime VII can be prepared by reacting methyl 2-methylphenylglyoxylate VI, for example, a) with O-methylhydroxylamine hydrochloride or b) with hydroxylamine hydrochloride to give the corresponding oxime, and reacting the latter with a methylating agent of the formula CH$_3$-L, in which L is a leaving group (for example chloride, bromide, iodide or methylsulfate) (cf. EP 253,213).

Methyl 2-methylphenylglyoxylate O-methyl oxime VII can also be prepared by oximating methyl 2-methylphenylacetate in a manner known per se (cf., for example, Houben-Weyl, Methoden der organischen Chemie [Methods of Organic Chemistry], Volume 10/4, pp. 28-32, Thieme Verlag, Stuttgart 1968) using an alkyl nitrite, such as, for example, ethyl nitrite, tert.-butyl nitrite or isoamyl nitrite, in the presence of a suitable base, such as, for example, sodium ethylate, potassium ethylate or potassium tert.-butylate, and alkylating the methyl 2-methylphenylglyoxylate oxime obtained in this way as described above.

The benzyl bromide VIII can be prepared by known methods by reacting the compound VII for example with bromine in a solvent, such as, for example, tetrachloromethane, if necessary with irradiation using a light source (for example Hg vapor lamp, 300 W) or with N-bromosuccinimide (Horner, Winkelmann, Angew. Chem. 71, 349 (1959)).

The novel compounds of the general formula I according to claim 1 are prepared, for example, by reacting an appropriately substituted phenol with the benzyl bromide VIII.

The reactions can be carried out, for example, in an inert solvent or diluent (for example acetone, acetonitrile, dimethyl sulfoxide, dimethylformamide, N-methylpyrrolidone, N,N'-dimethylpropyleneurea or pyridine) using a base (for example sodium carbonate or potassium carbonate). In addition, it may be advantageous to add a catalyst, such as, for example, tris-(3,6-dioxoheptyl)amine, to the reaction mixture.

Alternatively, a procedure may also be adopted in which the phenols are first converted using a base (for example sodium hydroxide, potassium hydroxide or sodium methanolate) into the corresponding sodium or potassium phenolates and the latter are then reacted with the benzyl bromide VIII in an inert solvent or diluent (for example dimethylformamide) to form the compounds of the general formula I.

The corresponding reactions can also be carried out in a two-phase system (for example tetrachloromethane/water). Suitable phase-transfer catalysts are, for example, trioctylpropylammonium chloride or cetyltrimethylammonium chloride.

The novel compounds of the general formula I can also be prepared in accordance with scheme 2:

Scheme 2:

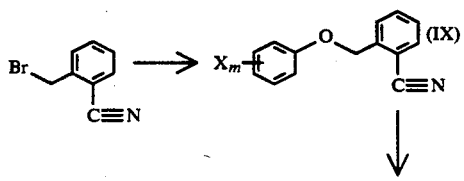

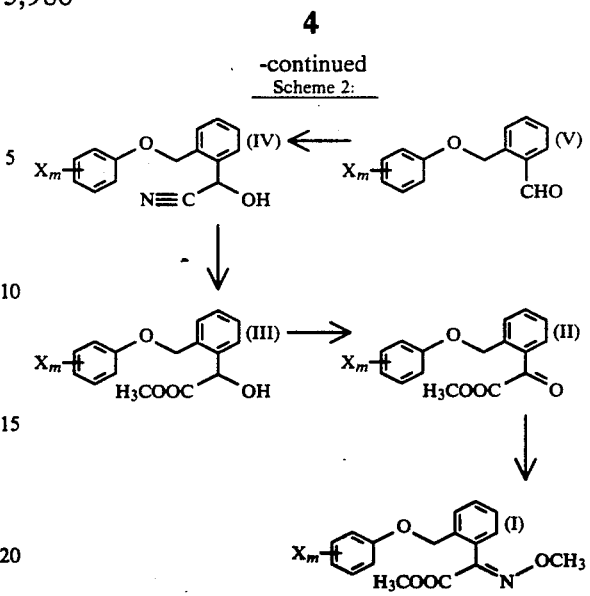

2-(Bromomethyl)benzonitrile is reacted with an appropriately substituted phenol to give the benzonitriles of the formula IX.

The reactions may be carried out, for example, in an inert solvent or diluent (for example acetone, dimethyl sulfoxide, dimethylformamide, N-methylpyrrolidone, N,N'-dimethylpropyleneurea or pyridine) using a base (for example sodium carbonate or potassium carbonate). In addition, it may be advantageous to add a catalyst, such as, for example, tris-(3,6-dioxoheptyl)amine, to the reaction mixture.

Alternatively, a procedure may be adopted in which the phenols are first converted using a base (for example sodium hydroxide, potassium hydroxide or sodium methanolate) into the corresponding sodium or potassium phenolates, and the latter are then reacted with 2-(bromomethyl)benzonitrile in an inert solvent or diluent (for example dimethylformamide).

The corresponding reactions can also be carried out in a two-phase system (for example tetrachloromethane/water). Suitable phase-transfer catalysts are, for example, trioctylpropylammonium chloride or cetyltrimethylammonium chloride.

Benzonitriles of the general formula IX are reduced to the benzaldehyde derivatives of the general formula V.

The reduction is carried out, for example, using hydrochloric acid/tin(II) chloride (Stephen reduction, cf., for example, Zil'berman, Pyryalova, J. Gen. Chem. USSR 33, (1964) 3348) or using a metal hydride, such as, for example, lithium aluminum or diisobutylaluminum hydride (cf., for example, Marshall, Andersen, Schlicher, J. Org. Chem. 35, (1970) 858).

The compounds of the general formula V are novel and are likewise covered by this invention.

Benzaldehyde cyanohydrins of the general formula IV can be prepared from the aldehydes of the general formula V in a generally known manner, for example using potassium cyanide or sodium cyanide.

The compounds of the general formula IV are novel and are likewise covered by this invention. In the presence of methanol and a protic acid, such as, for example, hydrochloric acid, they can be converted into the mandelates of the general formula III (cf., for example, U.S. Pat. No. 2,892,847).

The compounds of the general formula III are novel and are likewise covered by this invention. Reaction of them with a suitable oxidant, such as, for example, sodium hypochlorite, if necessary in the presence of an appropriate catalyst, such as tetrabutylammonium bisulfate, tetrabutylammonium bromide (cf., for example, EP 140,454) or tetramethylpiperidine N-oxide, gives methyl alpha-ketocarboxylates of the general formula II.

The compounds of the general formula II are novel and are likewise covered by this invention. From them, the compounds of the general structure I according to the invention can be synthesized in a known manner (cf. EP 253,213) by reaction, for example, a) with O-methylhydroxylamine hydrochloride or b) with hydroxylamine to form the corresponding oxime and reaction of the latter with a methylating agent of the formula $CH_3$-L, in which L is a leaving group (for example chloride, bromide or methylsulfate).

The examples and methods below are intended to illustrate the preparation of the novel active compounds and of the novel intermediates.

METHOD 1

2-Methylbenzaldehyde cyanohydrin 240 g of 2-methylbenzaldehyde, dissolved in 1000 ml of methyl tert.-butyl ether, are added dropwise to a solution of 245 g (3.75 mol) of potassium cyanide and 201 g (3.75 mol) of ammonium chloride in 800 ml of water.

The mixture is stirred at room temperature for 5 hours, and the organic phase is separated off. The aqueous phase is extracted three times with methyl tert.-butyl ether. The combined organic phases are dried and evaporated. 275 g of residue (GC: 85%) yield: 82%.

METHOD 2

Methyl 2-methylmandelate 275 g of the crude product from method 1 are dissolved in 750 ml of methanol, and the solution is added to 7.5 molar methanolic hydrochloric acid (620 ml). The mixture is stirred at room temperature for 15 hours. The pH is subsequently adjusted to 3 using NaOH/$H_2O$, and the mixture is stirred for a further 2 hours. The product is extracted using methylene chloride, and the extracts are dried and evaporated. 280.5 g of crude product (content of end product according to gas chromatography (GC) 76%) yield: 76%.

METHOD 3

Methyl 2-methylphenylglyoxylate (VI)

a) 230 g of the crude product from method 2 are dissolved in 230 g of ethyl acetate. 13.6 g of tetrabutylammonium bisulfate are added. 3.45 mol of sodium hypochlorite solution (NaOCl) are added dropwise with ice cooling. The mixture is stirred at room temperature overnight. The ethyl acetate phase is separated off, dried and evaporated. 202 g of crude product (GC 91%) are obtained. Yield: 85%.

b) 30 g (0.168 mol) of 2-methylbenzoyl cyanide are added to a mixture of 1.73 g (0.017 mol) of NaBr and 50 ml of 85% strength $H_2SO_4$. The mixture is heated to 70° C., 100 ml of methanol are added, and the mixture is heated at this temperature for a further 3 hours. After cooling, the mixture is extracted with toluene. The organic phase is washed with water until neutral, dried and evaporated. Distillation (92° C., 0.1 mbar) gives 22 g (yield 73%, GC: 87% purity) of crude product.

METHOD 4

Methyl 2-methylphenylglyoxylate O-methyl oxime a) 202 g of the crude product from method 3 are dissolved in 1500 g of methanol. 94 g of 2-methylhydroxylamine hydrochloride are added, and the mixture is refluxed for 9 hours. The mixture is taken up in ethyl acetate, and the organic phase is separated off, dried and evaporated. The residue is recrystallized from methyl tert.-butyl ether/hexane. 10 (Yield 65%, m.p. =65°–66° C.).

b) 195 g of 2-methylbenzoyl cyanide are added to 325 ml of 85% strength $H_2SO_4$ and 18.5 g of sodium bromide, the mixture is heated to 70° C., and 650 ml of methanol are added dropwise. The reaction mixture is stirred at this temperature for 3 hours. A solution of 114 g of 2-methylhydroxylamine hydrochloride in 2000 ml of methanol is subsequently added, and the mixture is refluxed for a further 9 hours. The solvent is removed, the residue is taken up in ethyl acetate, and the solution is washed with water, dried and evaporated. 237 g (yield 85%, GC 91%) of product are obtained.

c) A mixture of 200 g (1.22 mol) of methyl 2-methylphenylacetate and 377 g (3.66 mol) of tert.-butyl nitrite in 400 ml of tert.-butanol is added rapidly to 150 g (1.34 mol) of potassium tert.-butylate in 1500 ml of anhydrous tert.-butanol, the reaction temperature increasing to 70° C. After a few minutes, the potassium salt which forms begins to precipitate, and the reaction solution becomes difficult to stir. The mixture is stirred for a further one hour, and 261 g (1.84 mol) of methyl iodide are added in one portion. The potassium salt slowly dissolves, and microcrystalline potassium iodide precipitates. The mixture is stirred at room temperature overnight and evaporated, the residue is taken up in methyl tert.-butyl ether/$H_2O$, and the solution is washed several times with $H_2O$, dried over sodium sulfate and re-evaporated. The residue obtained is dissolved in warm isopropanol. $H_2O$ is added until the turbidity has just disappeared, and the product is then allowed to crystallize out at 0° C. 114 g (45%, m.p. =65°–66° C.) of product are obtained.

METHOD 5

Methyl 2-(bromomethyl)phenylglyoxylate O-methyl oxime (VIII) 21.4 g (0.133 mol) of bromine are added with stirring to 27.5 g (0.133 mol) of methyl 2-methylphenylglyoxylate O-methyl oxime dissolved in 400 ml of tetrachloromethane. The mixture is then heated at the reflux temperature for four hours while being irradiated with a 300 W Hg vapor lamp. The mixture is then evaporated, the residue is taken up in ethyl acetate/water, and the solution is washed with $H_2O$, dried using sodium sulfate and evaporated. The crude product is purified by chromatography on silica gel using cyclohexane/ethyl acetate (9/1). 17.4 g (46%) of the abovementioned compound are obtained as an oil.

METHOD 6

2(2,4-Dimethylphenoxymethyl)benzonitrile 382.5 g (2.65 mol) of sodium 2,4-dimethylphenolate and 100 mg of potassium iodide are dissolved in 1.5 l of N,N-dimethylformamide. 400 g (2.04 mol) of 2-bromomethylbenzonitrile are added in portions. The mixture is stirred at 40° C. for 16 hours and then evaporated, the residue is taken up in ethyl acetate, and the solution is washed with H₂O, dried over sodium sulfate and evaporated. The crude product is purified by stirring with a little n-pentene. 340 g (70%) of ochre crystals (m.p.=75°-76° C.) are obtained.

¹H NMR (CDCl₃):δ=2.24 (s, 3H), 2.26 (s, 3H), 5.17 (s, 2H), 6.76 (d, 1H), 6.95 (m, 2H), 7.35 (t, 1H), 7.62 (m, 3H)

METHOD 7

2-(2,4-Dimethylphenoxymethyl)benzaldehyde (Table 2, No. 2.62)

100 g (0.42 mol) of 2-(2,4-dimethylphenoxymethyl)-benzonitrile are added under nitrogen to 750 ml of absolute toluene, and 71 g (0.53 mol) of a 1.5 molar solution of diisobutylaluminum hydride are added slowly at 25° C. After the mixture has been stirred for 4 hours, first 70 ml of methanol and then 585 ml of 10% strength aqueous HCl solution are added dropwise with cooling in an ice bath. After the mixture has been stirred for a further 12 hours, the organic phase is separated off, dried over sodium sulfate and evaporated to give 100 g (99%) of brownish crystals (m.p. =70°-71° C.).

¹H NMR (CDCl₃): δ=2.25 (s, 3H), 2.29 (s, 3H), 5.49 (s, 2H), 6.8-7.1 (m, 3H), 7.4-8.0 (m, 4H), 10.2 (s, 1H)

METHOD 8

2-(2,4-Dimethylphenoxymethyl)benzaldehyde cyanohydrin (Table 3, No. 3.62)

47.6 g 0.73 mol) of potassium cyanide and 39.5 g (0.73 mol) of ammonium chloride are added to 220 ml of H₂O, and a solution of 92 g (0.38 mol) of 2-(2,4-dimethylphenoxymethyl)benzaldehyde in 425 ml of ether is added at 20 ° C. The mixture is stirred for 4 days and extracted thoroughly by shaking with ether. The combined ether phases are washed with H₂O, dried over sodium sulfate and evaporated. 95 g of the cyanohydrin are obtained as a crude product (80% purity), which is reacted further without further purification.

¹H NMR (CDCl₃):δ=2.2 (s, 3H), 2.3 (s, 3H), 3.95 (s, OH), 5.05 (d, 1H), 5 35 (d, 1H), 5.75 (s, 1H), 6.8-7.9 (m, 7H)

METHOD 9

Methyl 2-(2,4-Dimethylphenoxymethyl)mandelate (Table 4, No. 4.62)

0.3 mol of 2-(2,4-dimethylphenoxymethyl)benzaldehyde cyanohydrin and 0.6 mol of methanol are added to 850 ml of absolute ether. A solution of 0.35 mol of HCl gas in 250 ml of absolute ether is added dropwise at 0° C. The mixture is stirred at 0° C. for about 12 hours. The crystals which have precipitated are separated off, dissolved in 200 ml of H₂O and heated at the reflux temperature for 15 minutes. After cooling, the mixture is extracted several times with ether. The combined ether phases are washed with H₂O, dried over sodium sulfate and evaporated. The crude product is purified over a flash column (cyclohexane/ethyl acetate =8/2), to give 7 g (7%) of an oil.

¹H NMR (CDCl₃):δ=2.25 (s, 3H), 2.30 (s, 3H), 3.5 (s, . . H), 5.15 (s, 2H), 5.5 (s, 1H), 6.8-76.5 (m, 7H)

METHOD 10

Methyl 2-(2,4-Dimethylphenoxymethyl)phenylglyoxylate (Table 5, No. 5.62)

0.14 mol of methyl 2-(2,4-dimethylphenoxymethyl)-mandelate, 1.14 g of N,N-tetramethylpiperidine N-oxide, 0.8 g of potassium bromide, 2.5 g of Na₂HPO₄×2H₂O and 2.2 g of NaH₂PO₄×2H₂O are added to a mixture of 150 ml each of H₂O and dichloromethane. 0.168 mol of a sodium hypochlorite solution in H₂O is added dropwise with stirring at room temperature and pH 6-9. The aqueous phase is extracted twice with dichloromethane. The combined organic phases are dried over sodium sulfate and evaporated. The glyoxylate desired is obtained as an oil in quantitative yield.

¹H NMR (CDCl₃):δ=2.6 (s, 6H), 3.85 (s, 3H), 5.35 (s, 2H), 6.7-7.0 (m, 3H), 7.3-7.8 (m, 4H)

EXAMPLE 1

Methyl 2-(2,4-dimethylphenoxymethyl)phenylglyoxylate O-methyl oxime (Table 1, No. 1.62)

86 g (0.6 mol) of sodium 2,4-dimethylphenolate and about 0.5 g of potassium iodide are added to 1000 ml of N,N-dimethylformamide at room temperature, and 172 g (0.6 mol) of the bromomethyl compound VIII, dissolved in 300 ml of N,N-dimethylformamide, are added with stirring. The mixture is stirred at 100° C. for 8 hours and subsequently evaporated. The residue is taken up in ethyl acetate, and the solution is washed several times with H₂O, dried over sodium sulfate and evaporated. The crude product is stirred with n-pentane, the mixture is filtered with suction, and the product is dried. 125 g (84%, m.p. =68-74° C.) of the compound are obtained as white crystals.

¹H NMR (CDCl₃): δ=2.22 (s, 3H), 2.24 (s, 3H), 3.83 (s, 3H), 4.05 (s, 3H), 4.95 (s, 2H), 6.60-7.60 (m, 7H)

TABLE 1

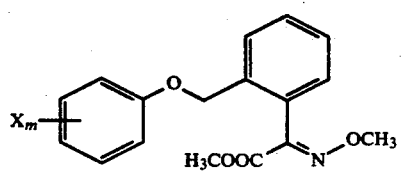

I

| No. | X_m | mp (°C.) | IR(cm⁻¹) |
|---|---|---|---|
| 1. 1 | 3-F | 72-75 | 2945, 1728, 1593, 1490, 1220, 1135, 1070, 1020 |
| 1. 2 | 4-F | 74-76 | 2970, 1733, 1726, 1508, 1222, 1204, 1070, 1016 |
| 1. 3 | 2,4-F₂ | 75-76 | 2960, 1738, 1515, 1267, 1212, 1068, 1007, 768 |

TABLE 1-continued

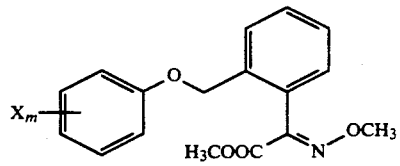

| No. | $X_m$ | mp (°C.) | IR(cm$^{-1}$) |
|---|---|---|---|
| 1.4 | 2,4,6-F$_3$ | | |
| 1.5 | 2,3,4,5,6-F$_5$ | | |
| 1.6 | 2,3-F$_2$ | | |
| 1.7 | 2,3-Cl$_2$ | 105–108 | 2955, 1743, 1456, 1303, 1068, 1015, 769 |
| 1.8 | 2,5-Cl$_2$ | 145–147 | 2945, 1738, 1583, 1379, 1301, 1248, 1069, 1009 |
| 1.9 | 2,6-Cl$_2$ | 115–118 | 2945, 1729, 1444, 1250, 1061, 1009, 772 |
| 1.10 | 3,4-Cl$_2$ | 90–92 | 2950, 1740, 1591, 1468, 1300, 1225, 1070, 1013 |
| 1.11 | 3,5-Cl$_2$ | 115–117 | 3080, 2945, 1743, 1587, 1573, 1306, 1070, 1008 |
| 1.12 | 2,3,4-Cl$_3$ | | |
| 1.13 | 2,3,5-Cl$_3$ | | |
| 1.14 | 2,3,6-Cl$_3$ | | |
| 1.15 | 2,4,5-Cl$_3$ | | |
| 1.16 | 2,4,6-Cl$_3$ | | |
| 1.17 | 3,4,5-Cl$_3$ | | |
| 1.18 | 2,3,4,6-Cl$_4$ | | |
| 1.19 | 2,3,5,6-Cl$_4$ | | |
| 1.20 | 2,3,4,5,6-Cl$_5$ | | |
| 1.21 | 2-Br | 94–97 | 2950, 1729, 1479, 1241, 1065, 1018, 746 |
| 1.22 | 3-Br | 66–67 | 2945, 1738, 1595, 1307, 1245, 1228, 1069, 1010 |
| 1.23 | 4-Br | 94–96 | 2945, 1739, 1486, 1286, 1231, 1067, 1008, 824 |
| 1.24 | 2,4-Br$_2$ | 106–108 | 2950, 1727, 1474, 1278, 1224, 1066, 1014 |
| 1.25 | 2,5-Br$_2$ | | |
| 1.26 | 2,6-Br$_2$ | | |
| 1.27 | 2,4,6-Br$_3$ | | |
| 1.28 | 2,3,4,5,6-Br$_5$ | | |
| 1.29 | 2-I | 80–83 | 2950, 1715, 1442, 1222, 1069, 1012, 744 |
| 1.30 | 3-I | | |
| 1.31 | 4-I | | |
| 1.32 | 2,4-I$_2$ | | |
| 1.33 | 2-Cl, 3-F | | |
| 1.34 | 2-Cl, 4-F | 73–75 | 2950, 1741, 1503, 1302, 1197, 1069, 1009, 791 |
| 1.35 | 2-Cl, 5-F | | |
| 1.36 | 2-Cl, 6-F | | |
| 1.37 | 2-Cl, 3-Br | | |
| 1.38 | 2-Cl, 4-Br | 114–116 | 2945, 1728, 1479, 1435, 1264, 1243, 1067, 1015 |
| 1.39 | 2-Cl, 5-Br | | |
| 1.40 | 2-Cl, 6-Br | | |
| 1.41 | 2-Br, 3-Cl | | |
| 1.42 | 2-Br, 4-Cl | 117–120 | 2940, 1723, 1479, 1441, 1218, 1067, 1021, 791 |
| 1.43 | 2-Br, 3-F | | |
| 1.45 | 2-Br, 4-F | 81–84 | 2960, 1725, 1498, 1434, 1265, 1197, 1068, 1013 |
| 1.46 | 2-Br, 5-F | | |
| 1.47 | 2-Br, 6-F | | |
| 1.48 | 2-F, 3-Cl | | |
| 1.49 | 2-F, 4-Cl | | |
| 1.50 | 2-F, 5-Cl | | |
| 1.51 | 3-Cl, 4-F | 86–89 | 2945, 1725, 1499, 1227, 1213, 1069, 1011, 785 |
| 1.52 | 3-Cl, 5-F | | |
| 1.53 | 3-Cl, 4-Br | | |
| 1.54 | 3-Cl, 5-Br | | |
| 1.55 | 3-F, 4-Cl | | |
| 1.56 | 3-F, 4-Br | | |
| 1.57 | 3-Br, 4-Cl | | |
| 1.58 | 3-Br, 4-F | | |
| 1.59 | 2,6-Cl$_2$, 4-Br | | |
| 1.60 | 3-CH$_3$ | 72 | 2950, 1729, 1256, 1152, 1066, 1010, 779 |
| 1.61 | 2,3-(CH$_3$)$_2$ | 110–113 | 2945, 1740, 1467, 1302, 1256, 1062, 1013, 771 |
| 1.62 | 2,4-(CH$_3$)$_2$ | 68–74 | 2945, 1739, 1504, 1253, 1223, 1065, 1005, 769 |
| 1.63 | 2,5-(CH$_3$)$_2$ | 103–105 | |
| 1.64 | 2,6-(CH$_3$)$_2$ | 85–88 | 1741, 1438, 1297, 1230, 1196, 1068, 1012, 997, 773 |
| 1.65 | 3,4-(CH$_3$)$_2$ | 89–93 | 1724, 1502, 1251, 1225, 1203, 1163, 1067, 1030, 1012, 954 |
| 1.66 | 3,5-(CH$_3$)$_2$ | 80–83 | 1739, 1594, 1322, 1302, 1222, 1152, 1078, 1065, 1009, 825 |
| 1.67 | 2,3,4-(CH$_3$)$_3$ | | |
| 1.68 | 2,3,5-(CH$_3$)$_3$ | 97–98 | 2940, 1740, 1300, 1219, 1067, 1008, 774 |
| 1.69 | 2,3,6-(CH$_3$)$_3$ | | |
| 1.70 | 2,4,5-(CH$_3$)$_3$ | 94–95 | |
| 1.71 | 2,4,6-(CH$_3$)$_3$ | 113–115 | |
| 1.72 | 3,4,5-(CH$_3$)$_3$ | 94–97 | 2960, 1719, 1441, 1317, 1223, 1145, 1065, 1020 |
| 1.73 | 2,3,4,6-(CH$_3$)$_4$ | | |
| 1.74 | 2,3,5,6-(CH$_3$)$_4$ | | |
| 1.75 | 2,3,4,5,6-(CH$_3$)$_5$ | | |
| 1.76 | 2-C$_2$H$_5$ | 46–48 | 2960, 1739, 1493, 1435, 1222, 1067, 748 |

TABLE 1-continued

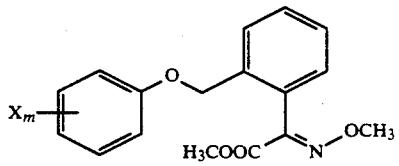

| No. | $X_m$ | mp (°C.) | IR(cm$^{-1}$) |
|---|---|---|---|
| 1.77 | 3-C$_2$H$_5$ | | |
| 1.78 | 4-C$_2$H$_5$ | | |
| 1.79 | 2,4-(C$_2$H$_5$)$_2$ | | |
| 1.80 | 2,6-(C$_2$H$_5$)$_2$ | | |
| 1.81 | 3,5-(C$_2$H$_5$)$_2$ | oil | 2963, 1727, 1592, 1455, 1339, 1285, 1218, 1152, 1069, 1020 |
| 1.82 | 2,4,6-(C$_2$H$_5$)$_3$ | | |
| 1.83 | 2-n-C$_3$H$_7$ | 44–46 | 2955, 1727, 1492, 1321, 1221, 1069, 1019, 752 |
| 1.84 | 3-n-C$_3$H$_7$ | | |
| 1.85 | 4-n-C$_3$H$_7$ | | |
| 1.86 | 2-i-C$_3$H$_7$ | oil | 2950, 1727, 1491, 1233, 1223, 1069, 1019, 753 |
| 1.87 | 3-i-C$_3$H$_7$ | | |
| 1.88 | 4-i-C$_3$H$_7$ | oil | 2958, 1728, 1512, 1222, 1070, 1019 |
| 1.89 | 2,4-(i-C$_3$H$_7$)$_2$ | oil | 2956, 1728, 1498, 1216, 1069, 1020 |
| 1.90 | 2,6-(i-C$_3$H$_7$)$_2$ | | |
| 1.91 | 3,5-(i-C$_3$H$_7$)$_2$ | oil | 2960, 1728, 1594, 1447, 1219, 1069, 1021 |
| 1.92 | 2,4,6-(i-C$_3$H$_7$)$_3$ | | |
| 1.93 | 2-s-C$_4$H$_9$ | oil | 2960, 1727, 1490, 1448, 1438, 1221, 1069, 1047, 1019, 752 |
| 1.94 | 3-s-C$_4$H$_9$ | | |
| 1.95 | 4-s-C$_4$H$_9$ | | |
| 1.96 | 2-t-C$_4$H$_9$ | | |
| 1.97 | 3-t-C$_4$H$_9$ | oil | 2962, 1728, 1582, 1437, 1274, 1219, 1069, 1020 |
| 1.98 | 2,3-(t-C$_4$H$_9$)$_2$ | | |
| 1.99 | 2,4-(t-C$_4$H$_9$)$_2$ | | |
| 1.100 | 2,5-(t-C$_4$H$_9$)$_2$ | | |
| 1.101 | 2,6-(t-C$_4$H$_9$)$_2$ | | |
| 1.102 | 3,5-(t-C$_4$H$_9$)$_2$ | oil | 2963, 1729, 1592, 1302, 1219, 1070, 1020 |
| 1.103 | 2,4,6-(t-C$_4$H$_9$)$_3$ | | |
| 1.104 | 4-n-C$_9$H$_{19}$ | oil | 2956, 2935, 2871, 1727, 1510, 1244, 1220, 1183, 1069, 1019 |
| 1.105 | 4-n-C$_{12}$H$_{25}$ | | |
| 1.106 | 3-n-C$_{15}$H$_{31}$ | | |
| 1.107 | 4-(1,1,3,3-tetramethylbutyl) | oil | 2954, 1728, 1511, 1317, 1303, 1245, 1220, 1183, 1069, 1020 |
| 1.108 | 4-(2,3,3-tri-methylpropyl) | | |
| 1.109 | 2-t-C$_4$H$_9$, 4-CH$_3$ | | |
| 1.110 | 2-t-C$_4$H$_9$, 5-CH$_3$ | | |
| 1.111 | 2,6-(t-C$_4$H$_9$)$_2$, 4-CH$_3$ | | |
| 1.112 | 2-CH$_3$, 4-t-C$_4$H$_9$ | | |
| 1.113 | 2-CH$_3$, 6-t-C$_4$H$_9$ | | |
| 1.114 | 2-CH$_3$, 4-i-C$_3$H$_7$ | | |
| 1.115 | 2-CH$_3$, 5-i-C$_3$H$_7$ | oil | 2957, 1727, 1437, 1252, 1218, 1069, 1020 |
| 1.116 | 3-CH$_3$, 4-i-C$_3$H$_7$ | | |
| 1.117 | 2-i-C$_3$H$_7$, 5-CH$_3$ | 70–74 | 2958, 1727, 1505, 1437, 1290, 1255, 1219, 1069, 1045, 1020 |
| 1.118 | 2,4-(t-C$_4$H$_9$)$_2$, 6-i-C$_3$H$_7$ | | |
| 1.119 | 2-C$_3$H$_5$ (= allyl) | 47 | 2945, 1739, 1493, 1304, 1251, 1069, 1010, 744 |
| 1.120 | 3-C$_3$H$_5$ | | |
| 1.121 | 4-C$_3$H$_5$ | | |
| 1.122 | 2-C$_3$H$_5$, 6-CH$_3$ | | |
| 1.123 | 2-cyclo-C$_6$H$_{11}$ | 115 | 2924, 1726, 1239, 1228, 1068, 1016, 750 |
| 1.124 | 3-cyclo-C$_6$H$_{11}$ | | |
| 1.125 | 4-cyclo-C$_6$H$_{11}$ | 93 | 2923, 1731, 1510, 1239, 1232, 1063, 1020, 822 |
| 1.126 | 2,4-(cyclo-C$_6$H$_{11}$)$_2$, 6-CH$_3$ | | |
| 1.127 | 2-CH$_3$, 4-cyclo-C$_6$H$_{11}$ | oil | 2925, 2851, 1727, 1504, 1218, 1070, 1020 |
| 1.128 | 2-CH$_2$C$_6$H$_5$ | | |
| 1.129 | 3-CH$_2$C$_6$H$_5$ | | |
| 1.130 | 4-CH$_2$C$_6$H$_5$ | | |
| 1.131 | 2-CH$_2$C$_6$H$_5$, 4-CH$_3$ | oil | 1726, 1501, 1495, 1452, 1249, 1220, 1069, 1019, 731 |
| 1.132 | 2-CH$_3$, 4-CH$_2$C$_6$H$_5$ | | |
| 1.133 | 2-C$_6$H$_5$ | oil | 1739, 1725, 1481, 1434, 1263, 1220, 1069, 1017, 754, 699 |
| 1.134 | 3-C$_6$H$_5$ | oil | 1726, 1477, 1320, 1300, 1219, 1202, 1069, 1017, 759, 698 |
| 1.135 | 4-C$_6$H$_5$ | resin | 2955, 1729, 1519, 1488, 1245, 1069, 1015, 765 |
| 1.136 | 4-(2-i-C$_3$H$_7$—C$_6$H$_4$) | | |
| 1.137 | 4-C$_6$H$_5$, 2,6-(CH$_3$)$_2$ | 138–142 | 1739, 1474, 1305, 1295, 1229, 11789, 1068, 1010, 1001, 768 |
| 1.138 | 2-Cl, 4-C$_6$H$_5$ | oil | 2945, 1726, 1596, 1477, 1301, 1202, 1069, 759 |
| 1.139 | 2-Br, 4-C$_6$H$_5$ | | |
| 1.140 | 2-C$_6$H$_5$, 4-Cl | | |
| 1.141 | 2-C$_6$H$_5$, 4-Br | | |
| 1.142 | 2-CH$_2$C$_6$H$_5$, 4-Cl | | |
| 1.143 | 2-CH$_2$C$_6$H$_5$, 4-Br | | |
| 1.144 | 2-Cl, 4-CH$_2$C$_6$H$_5$ | | |
| 1.145 | 2-Br, 4-CH$_2$C$_6$H$_5$ | | |
| 1.146 | 2-cyclo-C$_6$H$_{11}$, 4-Cl | | |
| 1.147 | 2-cyclo-C$_6$H$_{11}$, 4-Br | | |
| 1.148 | 2-Cl, 4-cyclo-C$_6$H$_{11}$ | | |

TABLE 1-continued

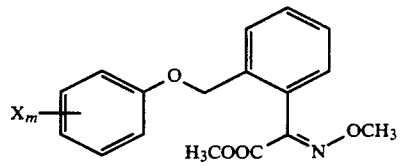

| No. | $X_m$ | mp (°C.) | IR(cm$^{-1}$) |
|---|---|---|---|
| 1. 149 | 2-Br, 4-cyclo-C$_6$H$_{11}$ | | |
| 1. 150 | 3-OCH$_3$ | 69-71 | 2945, 1719, 1589, 1200, 1153, 1069, 1012, 756 |
| 1. 151 | 2,4-(OCH$_3$)$_2$ | | |
| 1. 152 | 2-CF$_3$ | | |
| 1. 153 | 3-CF$_3$ | 46-48 | 2955, 1727, 1719, 1338, 1323, 1102, 1067, 1014 |
| 1. 154 | 4-CF$_3$ | | |
| 1. 155 | 2-OCF$_3$ | | |
| 1. 156 | 3-OCF$_3$ | | |
| 1. 157 | 4-OCF$_3$ | resin | 2950, 1731, 1506, 1242, 1222, 1119, 1069, 1017 |
| 1. 158 | 3-OCH$_2$CHF$_2$ | | |
| 1. 159 | 2-NO$_2$ | | |
| 1. 160 | 3-NO$_2$ | resin | |
| 1. 161 | 2-CN | 103-105 | 2945, 2230, 1728, 1450, 1254, 1062, 1010, 762 |
| 1. 162 | 3-CN | | |
| 1. 163 | 4-CN | | |
| 1. 164 | 2-CH$_3$, 3-Cl | | |
| 1. 165 | 2-CH$_3$, 5-Cl | | |
| 1. 166 | 2-CH$_3$, 6-Cl | | |
| 1. 167 | 2-CH$_3$, 3-F | | |
| 1. 168 | 2-CH$_3$, 4-F | | |
| 1. 169 | 2-CH$_3$, 5-F | | |
| 1. 170 | 2-CH$_3$, 6-F | | |
| 1. 171 | 2-CH$_3$, 3-Br | | |
| 1. 172 | 2-CH$_3$, 4-Br | | |
| 1. 173 | 2-CH$_3$, 5-Br | | |
| 1. 174 | 2-CH$_3$, 6-Br | | |
| 1. 175 | 2-Cl, 3-CH$_3$ | | |
| 1. 176 | 2-Cl, 4-CH$_3$ | 90-92 | 1726, 1500, 1437, 1298, 1285, 1251, 1218, 1068, 1017 |
| 1. 177 | 2-Cl, 5-CH$_3$ | 120-122 | 2940, 1737, 1489, 1309, 1070, 1065, 1008, 810 |
| 1. 178 | 2-F, 3-CH$_3$ | | |
| 1. 179 | 2-F, 4-CH$_3$ | | |
| 1. 180 | 2-F, 5-CH$_3$ | | |
| 1. 181 | 2-Br, 3-CH$_3$ | | |
| 1. 182 | 2-Br, 4-CH$_3$ | | |
| 1. 183 | 3-CH$_3$, 4-Cl | | |
| 1. 184 | 3-CH$_3$, 5-Cl | | |
| 1. 185 | 2-Br, 5-CH$_3$ | | |
| 1. 186 | 3-CH$_3$, 4-F | | |
| 1. 187 | 3-CH$_3$, 5-F | | |
| 1. 188 | 3-CH$_3$, 4-Br | | |
| 1. 189 | 3-CH$_3$, 5-Br | | |
| 1. 190 | 3-F, 4-CH$_3$ | | |
| 1. 191 | 3-Cl, 4-CH$_3$ | | |
| 1. 192 | 3-Br, 4-CH$_3$ | | |
| 1. 193 | 2-Cl, 4,5-(CH$_3$)$_2$ | | |
| 1. 194 | 2-Br, 4,5-(CH$_3$)$_2$ | | |
| 1. 195 | 2-Cl, 3,5-(CH$_3$)$_2$ | | |
| 1. 196 | 2-Br, 3,5-(CH$_3$)$_2$ | | |
| 1. 197 | 2,6-Cl$_2$, 4-CH$_3$ | | |
| 1. 198 | 2,6-F$_2$, 4-CH$_3$ | | |
| 1. 199 | 2,6-Br$_2$, 4-CH$_3$ | | |
| 1. 200 | 2,4-Cl$_2$, 6-CH$_3$ | | |
| 1. 201 | 2,4-F$_2$, 6-CH$_3$ | | |
| 1. 202 | 2,4-Br$_2$, 6-CH$_3$ | | |
| 1. 203 | 2,6-(CH$_3$)$_2$, 4-F | | |
| 1. 204 | 2,6-(CH$_3$)$_2$, 4-Cl | 94-97 | 2950, 1721, 1441, 1323, 1220, 1200, 1065, 1013 |
| 1. 205 | 2,6-(CH$_3$)$_2$, 4-Br | resin | 2950, 1722, 1436, 1321, 1220, 1199, 1067, 1014 |
| 1. 206 | 3,5-(CH$_3$)$_2$, 4-F | | |
| 1. 207 | 3,5-(CH$_3$)$_2$, 4-Cl | | |
| 1. 208 | 3,5-(CH$_3$)$_2$, 4-Br | | |
| 1. 209 | 2,3,6-(CH$_3$)$_3$, 4-F | | |
| 1. 210 | 2,3,6-(CH$_3$)$_3$, 4-Cl | | |
| 1. 211 | 2,3,6-(CH$_3$)$_3$, 4-Br | | |
| 1. 212 | 2,4-(CH$_3$)$_2$, 6-F | | |
| 1. 213 | 2,4-(CH$_3$)$_2$, 6-Cl | | |
| 1. 214 | 2,4-(CH$_3$)$_2$, 6-Br | | |
| 1. 215 | 2-i-C$_3$H$_7$, 4-Cl, 5-CH$_3$ | oil | 2960, 1727, 1495, 1437, 1245, 1219, 1170, 1124, 1070, 1019 |
| 1. 216 | 2-Cl, 4-NO$_2$ | | |
| 1. 217 | 2-NO$_2$, 4-Cl | | |
| 1. 218 | 2-OCH$_3$, 5-NO$_2$ | | |
| 1. 219 | 2,4-Cl$_2$, 5-NO$_2$ | | |
| 1. 220 | 2,4-Cl$_2$, 6-NO$_2$ | | |

TABLE 1-continued

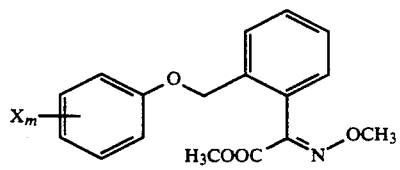

| No. | $X_m$ | mp (°C.) | IR(cm$^{-1}$) |
|---|---|---|---|
| 1. 221 | 2,6-Cl$_2$, 4-NO$_2$ | | |
| 1. 222 | 2,6-Br$_2$, 4-NO$_2$ | | |
| 1. 223 | 2,6-I$_2$, 4-NO$_2$ | | |
| 1. 224 | 2-CH$_3$, 5-i-C$_3$H$_7$, 4-Cl | oil | 2962, 1727, 1492, 1437, 1255, 1217, 1165, 1069, 1047, 1020 |
| 1. 225 | 2-C$_6$H$_5$O | | |
| 1. 226 | 3-C$_6$H$_5$O | | |
| 1. 227 | 4-C$_6$H$_5$O | | |
| 1. 228 | 3-t-C$_4$H$_9$O | | |
| 1. 229 | 4-t-C$_4$H$_9$O | | |
| 1. 230 | *1) | oil | 2945, 1726, 1400, 1269, 1097, 1069, 1019, 771 |
| 1. 231 | *2) | oil | 2950, 1727, 1441, 1214, 1177, 1066, 1012, 956 |
| 1. 232 | 4-OCH$_2$C$_6$H$_5$ | 130-133 | 2955, 1728, 1504, 1231, 1204, 1069, 1016, 741 |
| 1. 233 | 2-OC$_2$H$_5$ | | |
| 1. 234 | 2-CH$_3$, 4-(1,1,3,3-tetramethylbutyl) | oil | 2952, 2901, 1728, 1507, 1259, 1243, 1219, 1069, 1020 |
| 1. 235 | 2-Cl, 3-i-C$_3$H$_7$ | | |
| 1. 236 | 2-CH$_3$, 4-C$_6$H$_5$ | | |
| 1. 237 | 4-(1,1,3-trimethylbutyl) | | |
| 1. 238 | 3-CH$_3$, 5-i-C$_3$H$_7$ | oil | 2958, 1727, 1593, 1334, 1322, 1291, 1218, 1069, 1045, 1020 |
| 1. 239 | 2-CH$_3$, 4-cyclo-C$_5$H$_9$ | | |
| 1. 240 | 3-n-C$_4$H$_9$O | oil | 1727, 1591, 1492, 1284, 1219, 1179, 1152, 1069, 1044, 1019 |
| 1. 241 | 4-n-C$_4$H$_9$O | 66-67 | |
| 1. 242 | 3-n-C$_6$H$_{13}$O | oil | 2935, 1727, 1591, 1492, 1218, 1178, 1152, 1069, 1045, 1019 |
| 1. 243 | 4-n-C$_6$H$_{13}$O | 69-70 | |
| 1. 244 | 4-OC$_2$H$_5$ | 64-66 | 1722, 1512, 1438, 1241, 1216, 1118, 1069, 1047, 1030 |
| 1. 245 | 2-OCH$_3$, 4-CH$_3$ | oil | 1727, 1512, 1464, 1301, 1265, 1221, 1157, 1141, 1069, 1018 |
| 1. 246 | *3) | 82-86 | |

*1)
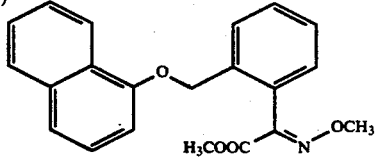

*2)
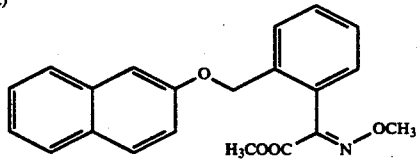

*3)
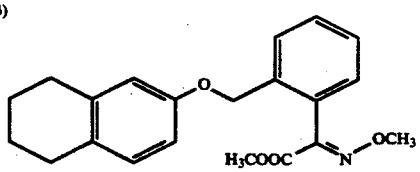

TABLE 2

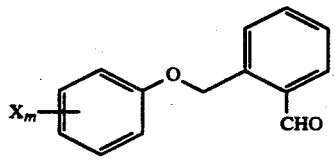
(V)

| No. | $X_m$ | mp (°C.) | IR(cm$^{-1}$) |
|---|---|---|---|
| 2. 1 | 3-F | | |
| 2. 2 | 4-F | | |
| 2. 3 | 2,4-F$_2$ | | |
| 2. 4 | 2,4,6-F$_3$ | | |
| 2. 5 | 2,3,4,5,6-F$_5$ | | |
| 2. 6 | 2,3-F$_2$ | | |

TABLE 2-continued

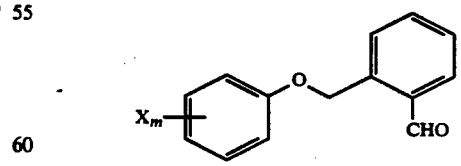
(V)

| No. | $X_m$ | mp (°C.) | IR(cm$^{-1}$) |
|---|---|---|---|
| 2. 7 | 2,3-Cl$_2$ | | |
| 2. 8 | 2,5-Cl$_2$ | | |
| 2. 9 | 2,6-Cl$_2$ | | |
| 2. 10 | 3,4-Cl$_2$ | | |
| 2. 11 | 3,5-Cl$_2$ | | |
| 2. 12 | 2,3,4-Cl$_3$ | | |

TABLE 2-continued (V)

[Structure: $X_m$—phenyl—O—CH$_2$—phenyl—CHO]

| No. | $X_m$ | mp (°C.) | IR(cm$^{-1}$) |
|---|---|---|---|
| 2. 13 | 2,3,5-Cl$_3$ | | |
| 2. 14 | 2,3,6-Cl$_3$ | | |
| 2. 15 | 2,4,5-Cl$_3$ | | |
| 2. 16 | 2,4,6-Cl$_3$ | | |
| 2. 17 | 3,4,5-Cl$_3$ | | |
| 2. 18 | 2,3,4,6-Cl$_4$ | | |
| 2. 19 | 2,3,5,6-Cl$_4$ | | |
| 2. 20 | 2,3,4,5,6-Cl$_5$ | | |
| 2. 21 | 2-Br | | |
| 2. 22 | 3-Br | | |
| 2. 23 | 4-Br | | |
| 2. 24 | 2,4-Br$_2$ | | |
| 2. 25 | 2,5-Br$_2$ | | |
| 2. 26 | 2,6-Br$_2$ | | |
| 2. 27 | 2,4,6-Br$_3$ | | |
| 2. 28 | 2,3,4,5,6-Br$_5$ | | |
| 2. 29 | 2-I | | |
| 2. 30 | 3-I | | |
| 2. 31 | 4-I | | |
| 2. 32 | 2,4-I$_2$ | | |
| 2. 33 | 2-Cl, 3-F | | |
| 2. 34 | 2-Cl, 4-F | | |
| 2. 35 | 2-Cl, 5-F | | |
| 2. 36 | 2-Cl, 6-F | | |
| 2. 37 | 2-Cl, 3-Br | | |
| 2. 38 | 2-Cl, 4-Br | | |
| 2. 39 | 2-Cl, 5-Br | | |
| 2. 40 | 2-Cl, 6-Br | | |
| 2. 41 | 2-Br, 3-Cl | | |
| 2. 42 | 2-Br, 4-Cl | | |
| 2. 43 | 2-Br, 3-F | | |
| 2. 45 | 2-Br, 4-F | | |
| 2. 46 | 2-Br, 5-F | | |
| 2. 47 | 2-Br, 6-F | | |
| 2. 48 | 2-F, 3-Cl | | |
| 2. 49 | 2-F, 4-Cl | | |
| 2. 50 | 2-F, 5-Cl | | |
| 2. 51 | 3-Cl, 4-F | | |
| 2. 52 | 3-Cl, 5-F | | |
| 2. 53 | 3-Cl, 4-Br | | |
| 2. 54 | 3-Cl, 5-Br | | |
| 2. 55 | 3-F, 4-Cl | | |
| 2. 56 | 3-F, 4-Br | | |
| 2. 57 | 3-Br, 4-Cl | | |
| 2. 58 | 3-Br, 4-F | | |
| 2. 59 | 2,6-Cl$_2$, 4-Br | | |
| 2. 60 | 3-CH$_3$ | | |
| 2. 61 | 2,3-(CH$_3$)$_2$ | | |
| 2. 62 | 2,4-(CH$_3$)$_2$ | 70-71 | 1855, 1685, 1502, 1254, 1223, 1131, 1033, 805, 764 |
| 2. 63 | 2,5-(CH$_3$)$_2$ | | |
| 2. 64 | 2,6-(CH$_3$)$_2$ | | |
| 2. 65 | 3,4-(CH$_3$)$_2$ | | |
| 2. 66 | 3,5-(CH$_3$)$_2$ | | |
| 2. 67 | 2,3,4-(CH$_3$)$_3$ | | |
| 2. 68 | 2,3,5-(CH$_3$)$_3$ | | |
| 2. 69 | 2,3,6-(CH$_3$)$_3$ | | |
| 2. 70 | 2,4,5-(CH$_3$)$_3$ | | |
| 2. 71 | 2,4,6-(CH$_3$)$_3$ | | |
| 2. 72 | 3,4,5-(CH$_3$)$_3$ | | |
| 2. 73 | 2,3,4,6-(CH$_3$)$_4$ | | |
| 2. 74 | 2,3,5,6-(CH$_3$)$_4$ | | |
| 2. 75 | 2,3,4,5,6-(CH$_3$)$_5$ | | |
| 2. 76 | 2-C$_2$H$_5$ | | |
| 2. 77 | 3-C$_2$H$_5$ | | |
| 2. 78 | 4-C$_2$H$_5$ | | |
| 2. 79 | 2,4-(C$_2$H$_5$)$_2$ | | |
| 2. 80 | 2,6-(C$_2$H$_5$)$_2$ | | |
| 2. 81 | 3,5-(C$_2$H$_5$)$_2$ | | |
| 2. 82 | 2,4,6-(C$_2$H$_5$)$_3$ | | |
| 2. 83 | 2-n-C$_3$H$_7$ | | |
| 2. 84 | 3-n-C$_3$H$_7$ | | |
| 2. 85 | 4-n-C$_3$H$_7$ | | |
| 2. 86 | 2-i-C$_3$H$_7$ | | |
| 2. 87 | 3-i-C$_3$H$_7$ | | |
| 2. 88 | 4-i-C$_3$H$_7$ | | |
| 2. 89 | 2,4-(i-C$_3$H$_7$)$_2$ | | |
| 2. 90 | 2,6-(i-C$_3$H$_7$)$_2$ | | |
| 2. 91 | 3,5-(i-C$_3$H$_7$)$_2$ | | |
| 2. 92 | 2,4,6-(i-C$_3$H$_7$)$_3$ | | |
| 2. 93 | 2-s-C$_4$H$_9$ | | |
| 2. 94 | 3-s-C$_4$H$_9$ | | |
| 2. 95 | 4-s-C$_4$H$_9$ | | |
| 2. 96 | 2-t-C$_4$H$_9$ | | |
| 2. 97 | 3-t-C$_4$H$_9$ | | |
| 2. 98 | 2,3-(t-C$_4$H$_9$)$_2$ | | |
| 2. 99 | 2,4-(t-C$_4$H$_9$)$_2$ | | |
| 2. 100 | 2,5-(t-C$_4$H$_9$)$_2$ | | |
| 2. 101 | 2,6-(t-C$_4$H$_9$)$_2$ | | |
| 2. 102 | 3,5-(t-C$_4$H$_9$)$_2$ | | |
| 2. 103 | 2,4,6-(t-C$_4$H$_9$)$_3$ | | |
| 2. 104 | 4-n-C$_9$H$_{19}$ | | |
| 2. 105 | 4-n-C$_{12}$H$_{25}$ | | |
| 2. 106 | 3-n-C$_{15}$H$_{31}$ | | |
| 2. 107 | 4-(1,1,3,3-tetramethylbutyl) | | |
| 2. 108 | 4-(2,3,3-trimethylpropyl) | | |
| 2. 109 | 2-t-C$_4$H$_9$, 4-CH$_3$ | | |
| 2. 110 | 2-t-C$_4$H$_9$, 5-CH$_3$ | | |
| 2. 111 | 2,6-(t-C$_4$H$_9$)$_2$, 4-CH$_3$ | | |
| 2. 112 | 2-CH$_3$, 4-t-C$_4$H$_9$ | | |
| 2. 113 | 2-CH$_3$, 6-t-C$_4$H$_9$ | | |
| 2. 114 | 2-CH$_3$, 4-i-C$_3$H$_7$ | | |
| 2. 115 | 2-CH$_3$, 5-i-C$_3$H$_7$ | | |
| 2. 116 | 3-CH$_3$, 4-i-C$_3$H$_7$ | | |
| 2. 117 | 2-i-C$_3$H$_7$, 5-CH$_3$ | | |
| 2. 118 | 2,4-(t-C$_4$H$_9$)$_2$, 6-i-C$_3$H$_7$ | | |
| 2. 119 | 2-C$_3$H$_5$ (= allyl) | | |
| 2. 120 | 3-C$_3$H$_5$ | | |
| 2. 121 | 4-C$_3$H$_5$ | | |
| 2. 122 | 2-C$_3$H$_5$, 6-CH$_3$ | | |
| 2. 123 | 2-cyclo-C$_6$H$_{11}$ | | |
| 2. 124 | 3-cyclo-C$_6$H$_{11}$ | | |
| 2. 125 | 4-cyclo-C$_6$H$_{11}$ | | |
| 2. 126 | 2,4-(cyclo-C$_6$H$_{11}$)$_2$, 6-CH$_3$ | | |
| 2. 127 | 2-CH$_3$, 4-cyclo-C$_6$H$_{11}$ | | |
| 2. 128 | 2-CH$_2$C$_6$H$_5$ | | |
| 2. 129 | 3-CH$_2$C$_6$H$_5$ | | |
| 2. 130 | 4-CH$_2$C$_6$H$_5$ | | |
| 2. 131 | 2-CH$_2$C$_6$H$_5$, 4-CH$_3$ | | |
| 2. 132 | 2-CH$_3$, 4-CH$_2$C$_6$H$_5$ | | |
| 2. 133 | 2-C$_6$H$_5$ | | |
| 2. 134 | 3-C$_6$H$_5$ | | |
| 2. 135 | 4-C$_6$H$_5$ | | |
| 2. 136 | 4-(2-i-C$_3$H$_7$—C$_6$H$_4$) | | |
| 2. 137 | 4-C$_6$H$_5$, 2,6-(CH$_3$)$_2$ | | |
| 2. 138 | 2-Cl, 4-C$_6$H$_5$ | | |
| 2. 139 | 2-Br, 4-C$_6$H$_5$ | | |
| 2. 140 | 2-C$_6$H$_5$, 4-Cl | | |
| 2. 141 | 2-C$_6$H$_5$, 4-Br | | |
| 2. 142 | 2-CH$_2$C$_6$H$_5$, 4-Cl | | |
| 2. 143 | 2-CH$_2$C$_6$H$_5$, 4-Br | | |
| 2. 144 | 2-Cl, 4-CH$_2$C$_6$H$_5$ | | |
| 2. 145 | 2-Br, 4-CH$_2$C$_6$H$_5$ | | |
| 2. 146 | 2-cyclo-C$_6$H$_{11}$, 4-Cl | | |
| 2. 147 | 2-cyclo-C$_6$H$_{11}$, 4-Br | | |
| 2. 148 | 2-Cl, 4-cyclo-C$_6$H$_{11}$ | | |
| 2. 149 | 2-Br, 4-cyclo-C$_6$H$_{11}$ | | |
| 2. 150 | 3-OCH$_3$ | | |
| 2. 151 | 2,4-(OCH$_3$)$_2$ | | |
| 2. 152 | 2-CF$_3$ | | |
| 2. 153 | 3-CF$_3$ | | |

TABLE 2-continued (V)

| No. | $X_m$ | mp (°C.) | IR(cm$^{-1}$) |
|---|---|---|---|
| 2. 154 | 4-CF$_3$ | | |
| 2. 155 | 2-OCF$_3$ | | |
| 2. 156 | 3-OCF$_3$ | | |
| 2. 157 | 4-OCF$_3$ | | |
| 2. 158 | 3-OCH$_2$CHF$_2$ | | |
| 2. 159 | 2-NO$_2$ | | |
| 2. 160 | 3-NO$_2$ | | |
| 2. 161 | 2-CN | | |
| 2. 162 | 3-CN | | |
| 2. 163 | 4-CN | | |
| 2. 164 | 2-CH$_3$, 3-Cl | | |
| 2. 165 | 2-CH$_3$, 5-Cl | | |
| 2. 166 | 2-CH$_3$, 6-Cl | | |
| 2. 167 | 2-CH$_3$, 3-F | | |
| 2. 168 | 2-CH$_3$, 4-F | | |
| 2. 169 | 2-CH$_3$, 5-F | | |
| 2. 170 | 2-CH$_3$, 6-F | | |
| 2. 171 | 2-CH$_3$, 3-Br | | |
| 2. 172 | 2-CH$_3$, 4-Br | | |
| 2. 173 | 2-CH$_3$, 5-Br | | |
| 2. 174 | 2-CH$_3$, 6-Br | | |
| 2. 175 | 2-Cl, 3-CH$_3$ | | |
| 2. 176 | 2-Cl, 4-CH$_3$ | | |
| 2. 177 | 2-Cl, 5-CH$_3$ | | |
| 2. 178 | 2-F, 3-CH$_3$ | | |
| 2. 179 | 2-F, 4-CH$_3$ | | |
| 2. 180 | 2-F, 5-CH$_3$ | | |
| 2. 181 | 2-Br, 3-CH$_3$ | | |
| 2. 182 | 2-Br, 4-CH$_3$ | | |
| 2. 183 | 3-CH$_3$, 4-Cl | | |
| 2. 184 | 3-CH$_3$, 5-Cl | | |
| 2. 185 | 2-Br, 5-CH$_3$ | | |
| 2. 186 | 3-CH$_3$, 4-F | | |
| 2. 187 | 3-CH$_3$, 5-F | | |
| 2. 188 | 3-CH$_3$, 4-Br | | |
| 2. 189 | 3-CH$_3$, 5-Br | | |
| 2. 190 | 3-F, 4-CH$_3$ | | |
| 2. 191 | 3-Cl, 4-CH$_3$ | | |
| 2. 192 | 3-Br, 4-CH$_3$ | | |
| 2. 193 | 2-Cl, 4,5-(CH$_3$)$_2$ | | |
| 2. 194 | 2-Br, 4,5-(CH$_3$)$_2$ | | |
| 2. 195 | 2-Cl, 3,5-(CH$_3$)$_2$ | | |
| 2. 196 | 2-Br, 3,5-(CH$_3$)$_2$ | | |
| 2. 197 | 2,6-Cl$_2$, 4-CH$_3$ | | |
| 2. 198 | 2,6-F$_2$, 4-CH$_3$ | | |
| 2. 199 | 2,6-Br$_2$, 4-CH$_3$ | | |
| 2. 200 | 2,4-Cl$_2$, 6-CH$_3$ | | |
| 2. 201 | 2,4-F$_2$, 6-CH$_3$ | | |
| 2. 202 | 2,4-Br$_2$, 6-CH$_3$ | | |
| 2. 203 | 2,6-(CH$_3$)$_2$, 4-F | | |
| 2. 204 | 2,6-(CH$_3$)$_2$, 4-Cl | | |
| 2. 205 | 2,6-(CH$_3$)$_2$, 4-Br | | |
| 2. 206 | 3,5-(CH$_3$)$_2$, 4-F | | |
| 2. 207 | 3,5-(CH$_3$)$_2$, 4-Cl | | |
| 2. 208 | 3,5-(CH$_3$)$_2$, 4-Br | | |
| 2. 209 | 2,3,6-(CH$_3$)$_3$, 4-F | | |
| 2. 210 | 2,3,6-(CH$_3$)$_3$, 4-Cl | | |
| 2. 211 | 2,3,6-(CH$_3$)$_3$, 4-Br | | |
| 2. 212 | 2,4-(CH$_3$)$_2$, 6-F | | |
| 2. 213 | 2,4-(CH$_3$)$_2$, 6-Cl | | |
| 2. 214 | 2,4-(CH$_3$)$_2$, 6-Br | | |
| 2. 215 | 2-i-C$_3$H$_7$, 4-Cl, 5-CH$_3$ | | |
| 2. 216 | 2-Cl, 4-NO$_2$ | | |
| 2. 217 | 2-NO$_2$, 4-Cl | | |
| 2. 218 | 2-OCH$_3$, 5-NO$_2$ | | |
| 2. 219 | 2,4-Cl$_2$, 5-NO$_2$ | | |
| 2. 220 | 2,4-Cl$_2$, 6-NO$_2$ | | |
| 2. 221 | 2,6-Cl$_2$, 4-NO$_2$ | | |
| 2. 222 | 2,6-Br$_2$, 4-NO$_2$ | | |
| 2. 223 | 2,6-I$_2$, 4-NO$_2$ | | |
| 2. 224 | 2-CH$_3$, 5-i-C$_3$H$_7$, 4-Cl | | |
| 2. 225 | 2-C$_6$H$_5$O | | |
| 2. 226 | 3-C$_6$H$_5$O | | |
| 2. 227 | 4-C$_6$H$_5$O | | |
| 2. 228 | 3-t-C$_4$H$_9$O | | |
| 2. 229 | 4-t-C$_4$H$_9$O | | |
| 2. 230 | *1) | | |
| 2. 231 | *2) | | |

*1) 1-naphthyloxy derivative

*2) 2-naphthyloxy derivative

TABLE 3

(IV)

| No. | $X_m$ | mp (°C.) | IR(cm$^{-1}$) |
|---|---|---|---|
| 3. 1 | 3-F | | |
| 3. 2 | 4-F | | |
| 3. 3 | 2,4-F$_2$ | | |
| 3. 4 | 2,4,6-F$_3$ | | |
| 3. 5 | 2,3,4,5,6-F$_5$ | | |
| 3. 6 | 2,3-F$_2$ | | |
| 3. 7 | 2,3-Cl$_2$ | | |
| 3. 8 | 2,5-Cl$_2$ | | |
| 3. 9 | 2,6-Cl$_2$ | | |
| 3. 10 | 3,4-Cl$_2$ | | |
| 3. 11 | 3,5-Cl$_2$ | | |
| 3. 12 | 2,3,4-Cl$_3$ | | |
| 3. 13 | 2,3,5-Cl$_3$ | | |
| 3. 14 | 2,3,6-Cl$_3$ | | |
| 3. 15 | 2,4,5-Cl$_3$ | | |
| 3. 16 | 2,4,6-Cl$_3$ | | |
| 3. 17 | 3,4,5-Cl$_3$ | | |
| 3. 18 | 2,3,4,6-Cl$_4$ | | |
| 3. 19 | 2,3,5,6-Cl$_4$ | | |
| 3. 20 | 2,3,4,5,6-Cl$_5$ | | |
| 3. 21 | 2-Br | | |
| 3. 22 | 3-Br | | |
| 3. 23 | 4-Br | | |
| 3. 24 | 2,4-Br$_2$ | | |
| 3. 25 | 2,5-Br$_2$ | | |
| 3. 26 | 2,6-Br$_2$ | | |
| 3. 27 | 2,4,6-Br$_3$ | | |
| 3. 28 | 2,3,4,5,6-Br$_5$ | | |
| 3. 29 | 2-I | | |
| 3. 30 | 3-I | | |
| 3. 31 | 4-I | | |
| 3. 32 | 2,4-I$_2$ | | |
| 3. 33 | 2-Cl, 3-F | | |

TABLE 3-continued (IV)

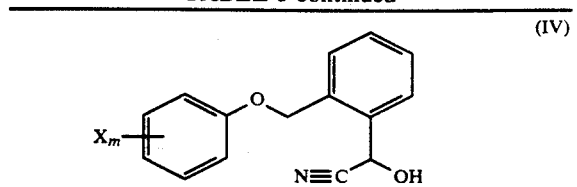

| No. | $X_m$ | mp (°C.) | IR(cm$^{-1}$) |
|---|---|---|---|
| 3.34 | 2-Cl, 4-F | | |
| 3.35 | 2-Cl, 5-F | | |
| 3.36 | 2-Cl, 6-F | | |
| 3.37 | 2-Cl, 3-Br | | |
| 3.38 | 2-Cl, 4-Br | | |
| 3.39 | 2-Cl, 5-Br | | |
| 3.40 | 2-Cl, 6-Br | | |
| 3.41 | 2-Br, 3-Cl | | |
| 3.42 | 2-Br, 4-Cl | | |
| 3.43 | 2-Br, 3-F | | |
| 3.45 | 2-Br, 4-F | | |
| 3.46 | 2-Br, 5-F | | |
| 3.47 | 2-Br, 6-F | | |
| 3.48 | 2-F, 3-Cl | | |
| 3.49 | 2-F, 4-Cl | | |
| 3.50 | 2-F, 5-Cl | | |
| 3.51 | 3-Cl, 4-F | | |
| 3.52 | 3-Cl, 5-F | | |
| 3.53 | 3-Cl, 4-Br | | |
| 3.54 | 3-Cl, 5-Br | | |
| 3.55 | 3-F, 4-Cl | | |
| 3.56 | 3-F, 4-Br | | |
| 3.57 | 3-Br, 4-Cl | | |
| 3.58 | 3-Br, 4-F | | |
| 3.59 | 2,6-Cl$_2$, 4-Br | | |
| 3.60 | 3-CH$_3$ | | |
| 3.61 | 2,3-(CH$_3$)$_2$ | | |
| 3.62 | 2,4-(CH$_3$)$_2$ | oil | 3422, 2910, 1504, 1255, 1220, 1133, 1035, 759 |
| 3.63 | 2,5-(CH$_3$)$_2$ | | |
| 3.64 | 2,6-(CH$_3$)$_2$ | | |
| 3.65 | 3,4-(CH$_3$)$_2$ | | |
| 3.66 | 3,5-(CH$_3$)$_2$ | | |
| 3.67 | 2,3,4-(CH$_3$)$_3$ | | |
| 3.68 | 2,3,5-(CH$_3$)$_3$ | | |
| 3.69 | 2,3,6-(CH$_3$)$_3$ | | |
| 3.70 | 2,4,5-(CH$_3$)$_3$ | | |
| 3.71 | 2,4,6-(CH$_3$)$_3$ | | |
| 3.72 | 3,4,5-(CH$_3$)$_3$ | | |
| 3.73 | 2,3,4,6-(CH$_3$)$_4$ | | |
| 3.74 | 2,3,5,6-(CH$_3$)$_4$ | | |
| 3.75 | 2,3,4,5,6-(CH$_3$)$_5$ | | |
| 3.76 | 2-C$_2$H$_5$ | | |
| 3.77 | 3-C$_2$H$_5$ | | |
| 3.78 | 4-C$_2$H$_5$ | | |
| 3.79 | 2,4-(C$_2$H$_5$)$_2$ | | |
| 3.80 | 2,6-(C$_2$H$_5$)$_2$ | | |
| 3.81 | 3,5-(C$_2$H$_5$)$_2$ | | |
| 3.82 | 2,4,6-(C$_2$H$_5$)$_3$ | | |
| 3.83 | 2-n-C$_3$H$_7$ | | |
| 3.84 | 3-n-C$_3$H$_7$ | | |
| 3.85 | 4-n-C$_3$H$_7$ | | |
| 3.86 | 2-i-C$_3$H$_7$ | | |
| 3.87 | 3-i-C$_3$H$_7$ | | |
| 3.88 | 4-i-C$_3$H$_7$ | | |
| 3.89 | 2,4-(i-C$_3$H$_7$)$_2$ | | |
| 3.90 | 2,6-(i-C$_3$H$_7$)$_2$ | | |
| 3.91 | 3,5-(i-C$_3$H$_7$)$_2$ | | |
| 3.92 | 2,4,6-(i-C$_3$H$_7$)$_3$ | | |
| 3.93 | 2-s-C$_4$H$_9$ | | |
| 3.94 | 3-s-C$_4$H$_9$ | | |
| 3.95 | 4-s-C$_4$H$_9$ | | |
| 3.96 | 2-t-C$_4$H$_9$ | | |
| 3.97 | 3-t-C$_4$H$_9$ | | |
| 3.98 | 2,3-(t-C$_4$H$_9$)$_2$ | | |
| 3.99 | 2,4-(t-C$_4$H$_9$)$_2$ | | |
| 3.100 | 2,5-(t-C$_4$H$_9$)$_2$ | | |
| 3.101 | 2,6-(t-C$_4$H$_9$)$_2$ | | |
| 3.102 | 3,5-(t-C$_4$H$_9$)$_2$ | | |
| 3.103 | 2,4,6-(t-C$_4$H$_9$)$_3$ | | |
| 3.104 | 4-n-C$_9$H$_{19}$ | | |
| 3.105 | 4-n-C$_{12}$H$_{25}$ | | |
| 3.106 | 3-n-C$_{15}$H$_{31}$ | | |
| 3.107 | 4-(1,1,3,3-tetramethylbutyl) | | |
| 3.108 | 4-(2,3,3-trimethylpropyl) | | |
| 3.109 | 2-t-C$_4$H$_9$, 4-CH$_3$ | | |
| 3.110 | 2-t-C$_4$H$_9$, 5-CH$_3$ | | |
| 3.111 | 2,6-(t-C$_4$H$_9$)$_2$, 4-CH$_3$ | | |
| 3.112 | 2-CH$_3$, 4-t-C$_4$H$_9$ | | |
| 3.113 | 2-CH$_3$, 6-t-C$_4$H$_9$ | | |
| 3.114 | 2-CH$_3$, 4-i-C$_3$H$_7$ | | |
| 3.115 | 2-CH$_3$, 5-i-C$_3$H$_7$ | | |
| 3.116 | 3-CH$_3$, 4-i-C$_3$H$_7$ | | |
| 3.117 | 2-i-C$_3$H$_7$, 5-CH$_3$ | | |
| 3.118 | 2,4-(t-C$_4$H$_9$)$_2$, 6-i-C$_3$H$_7$ | | |
| 3.119 | 2-C$_3$H$_5$ (= allyl) | | |
| 3.120 | 3-C$_3$H$_5$ | | |
| 3.121 | 4-C$_3$H$_5$ | | |
| 3.122 | 2-C$_3$H$_5$, 6-CH$_3$ | | |
| 3.123 | 2-cyclo-C$_6$H$_{11}$ | | |
| 3.124 | 3-cyclo-C$_6$H$_{11}$ | | |
| 3.125 | 4-cyclo-C$_6$H$_{11}$ | | |
| 3.126 | 2,4-(cyclo-C$_6$H$_{11}$)$_2$, 6-CH$_3$ | | |
| 3.127 | 2-CH$_3$, 4-cyclo-C$_6$H$_{11}$ | | |
| 3.128 | 2-CH$_2$C$_6$H$_5$ | | |
| 3.129 | 3-CH$_2$C$_6$H$_5$ | | |
| 3.130 | 4-CH$_2$C$_6$H$_5$ | | |
| 3.131 | 2-CH$_2$C$_6$H$_5$, 4-CH$_3$ | | |
| 3.132 | 2-CH$_3$, 4-CH$_2$C$_6$H$_5$ | | |
| 3.133 | 2-C$_6$H$_5$ | | |
| 3.134 | 3-C$_6$H$_5$ | | |
| 3.135 | 4-C$_6$H$_5$ | | |
| 3.136 | 4-(2-i-C$_3$H$_7$—C$_6$H$_4$) | | |
| 3.137 | 4-C$_6$H$_5$, 2,6-(CH$_3$)$_2$ | | |
| 3.138 | 2-Cl, 4-C$_6$H$_5$ | | |
| 3.139 | 2-Br, 4-C$_6$H$_5$ | | |
| 3.140 | 2-C$_6$H$_5$, 4-Cl | | |
| 3.141 | 2-C$_6$H$_5$, 4-Br | | |
| 3.142 | 2-CH$_2$C$_6$H$_5$, 4-Cl | | |
| 3.143 | 2-CH$_2$C$_6$H$_5$, 4-Br | | |
| 3.144 | 2-Cl, 4-CH$_2$C$_6$H$_5$ | | |
| 3.145 | 2-Br, 4-CH$_2$C$_6$H$_5$ | | |
| 3.146 | 2-cyclo-C$_6$H$_{11}$, 4-Cl | | |
| 3.147 | 2-cyclo-C$_6$H$_{11}$, 4-Br | | |
| 3.148 | 2-Cl, 4-cyclo-C$_6$H$_{11}$ | | |
| 3.149 | 2-Br, 4-cyclo-C$_6$H$_{11}$ | | |
| 3.150 | 3-OCH$_3$ | | |
| 3.151 | 2,4-(OCH$_3$)$_2$ | | |
| 3.152 | 2-CF$_3$ | | |
| 3.153 | 3-CF$_3$ | | |
| 3.154 | 4-CF$_3$ | | |
| 3.155 | 2-OCF$_3$ | | |
| 3.156 | 3-OCF$_3$ | | |
| 3.157 | 4-OCF$_3$ | | |
| 3.158 | 3-OCH$_2$CHF$_2$ | | |
| 3.159 | 2-NO$_2$ | | |
| 3.160 | 3-NO$_2$ | | |
| 3.161 | 2-CN | | |
| 3.162 | 3-CN | | |
| 3.163 | 4-CN | | |
| 3.164 | 2-CH$_3$, 3-Cl | | |
| 3.165 | 2-CH$_3$, 5-Cl | | |
| 3.166 | 2-CH$_3$, 6-Cl | | |
| 3.167 | 2-CH$_3$, 3-F | | |
| 3.168 | 2-CH$_3$, 4-F | | |
| 3.169 | 2-CH$_3$, 5-F | | |
| 3.170 | 2-CH$_3$, 6-F | | |
| 3.171 | 2-CH$_3$, 3-Br | | |
| 3.172 | 2-CH$_3$, 4-Br | | |
| 3.173 | 2-CH$_3$, 5-Br | | |
| 3.174 | 2-CH$_3$, 6-Br | | |
| 3.175 | 2-Cl, 3-CH$_3$ | | |

TABLE 3-continued

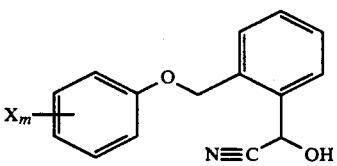
(IV)

| No. | $X_m$ | mp (°C.) | IR(cm$^{-1}$) |
|---|---|---|---|
| 3. 176 | 2-Cl, 4-CH$_3$ | | |
| 3. 177 | 2-Cl, 5-CH$_3$ | | |
| 3. 178 | 2-F, 3-CH$_3$ | | |
| 3. 179 | 2-F, 4-CH$_3$ | | |
| 3. 180 | 2-F, 5-CH$_3$ | | |
| 3. 181 | 2-Br, 3-CH$_3$ | | |
| 3. 182 | 2-Br, 4-CH$_3$ | | |
| 3. 183 | 3-CH$_3$, 4-Cl | | |
| 3. 184 | 3-CH$_3$, 5-Cl | | |
| 3. 185 | 2-Br, 5-CH$_3$ | | |
| 3. 186 | 3-CH$_3$, 4-F | | |
| 3. 187 | 3-CH$_3$, 5-F | | |
| 3. 188 | 3-CH$_3$, 4-Br | | |
| 3. 189 | 3-CH$_3$, 5-Br | | |
| 3. 190 | 3-F, 4-CH$_3$ | | |
| 3. 191 | 3-Cl, 4-CH$_3$ | | |
| 3. 192 | 3-Br, 4-CH$_3$ | | |
| 3. 193 | 2-Cl, 4,5-(CH$_3$)$_2$ | | |
| 3. 194 | 2-Br, 4,5-(CH$_3$)$_2$ | | |
| 3. 195 | 2-Cl, 3,5-(CH$_3$)$_2$ | | |
| 3. 196 | 2-Br, 3,5-(CH$_3$)$_2$ | | |
| 3. 197 | 2,6-Cl$_2$, 4-CH$_3$ | | |
| 3. 198 | 2,6-F$_2$, 4-CH$_3$ | | |
| 3. 199 | 2,6-Br$_2$, 4-CH$_3$ | | |
| 3. 200 | 2,4-Cl$_2$, 6-CH$_3$ | | |
| 3. 201 | 2,4-F$_2$, 6-CH$_3$ | | |
| 3. 202 | 2,4-Br$_2$, 6-CH$_3$ | | |
| 3. 203 | 2,6-(CH$_3$)$_2$, 4-F | | |
| 3. 204 | 2,6-(CH$_3$)$_2$, 4-Cl | | |
| 3. 205 | 2,6-(CH$_3$)$_2$, 4-Br | | |
| 3. 206 | 3,5-(CH$_3$)$_2$, 4-F | | |
| 3. 207 | 3,5-(CH$_3$)$_2$, 4-Cl | | |
| 3. 208 | 3,5-(CH$_3$)$_2$, 4-Br | | |
| 3. 209 | 2,3,6-(CH$_3$)$_3$, 4-F | | |
| 3. 210 | 2,3,6-(CH$_3$)$_3$, 4-Cl | | |
| 3. 211 | 2,3,6-(CH$_3$)$_3$, 4-Br | | |
| 3. 212 | 2,4-(CH$_3$)$_2$, 6-F | | |
| 3. 213 | 2,4-(CH$_3$)$_2$, 6-Cl | | |
| 3. 214 | 2,4-(CH$_3$)$_2$, 6-Br | | |
| 3. 215 | 2-i-C$_3$H$_7$, 4-Cl, 5-CH$_3$ | | |
| 3. 216 | 2-Cl, 4-NO$_2$ | | |
| 3. 217 | 2-NO$_2$, 4-Cl | | |
| 3. 218 | 2-OCH$_3$, 5-NO$_2$ | | |
| 3. 219 | 2,4-Cl$_2$, 5-NO$_2$ | | |
| 3. 220 | 2,4-Cl$_2$, 6-NO$_2$ | | |
| 3. 221 | 2,6-Cl$_2$, 4-NO$_2$ | | |
| 3. 222 | 2,6-Br$_2$, 4-NO$_2$ | | |
| 3. 223 | 2,6-I$_2$, 4-NO$_2$ | | |
| 3. 224 | 2-CH$_3$, 5-i-C$_3$H$_7$, 4-Cl | | |
| 3. 225 | 2-C$_6$H$_5$O | | |
| 3. 226 | 3-C$_6$H$_5$O | | |
| 3. 227 | 4-C$_6$H$_5$O | | |
| 3. 228 | 3-t-C$_4$H$_9$O | | |
| 3. 229 | 4-t-C$_4$H$_9$O | | |
| 3. 230 | *1) | | |

TABLE 3-continued

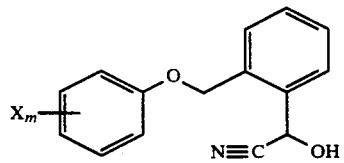
(IV)

| No. | $X_m$ | mp (°C.) | IR(cm$^{-1}$) |
|---|---|---|---|
| 3. 231 | *2) | | |

*1)
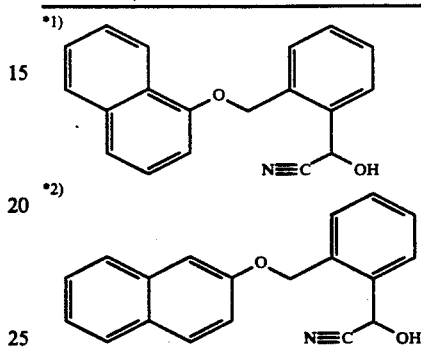

*2)
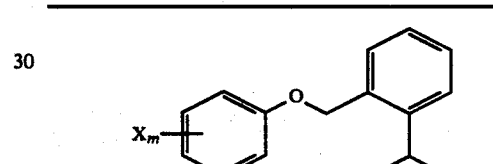

TABLE 4

(III)

| No. | $X_m$ | mp (°C.) | IR(cm$^{-1}$) |
|---|---|---|---|
| 4. 1 | 3-F | | |
| 4. 2 | 4-F | | |
| 4. 3 | 2,4-F$_2$ | | |
| 4. 4 | 2,4,6-F$_3$ | | |
| 4. 5 | 2,3,4,5,6-F$_5$ | | |
| 4. 6 | 2,3-F$_2$ | | |
| 4. 7 | 2,3-Cl$_2$ | | |
| 4. 8 | 2,5-Cl$_2$ | | |
| 4. 9 | 2,6-Cl$_2$ | | |
| 4. 10 | 3,4-Cl$_2$ | | |
| 4. 11 | 3,5-Cl$_2$ | | |
| 4. 12 | 2,3,4-Cl$_3$ | | |
| 4. 13 | 2,3,5-Cl$_3$ | | |
| 4. 14 | 2,3,6-Cl$_3$ | | |
| 4. 15 | 2,4,5-Cl$_3$ | | |
| 4. 16 | 2,4,6-Cl$_3$ | | |
| 4. 17 | 3,4,5-Cl$_3$ | | |
| 4. 18 | 2,3,4,6-Cl$_4$ | | |
| 4. 19 | 2,3,5,6-Cl$_4$ | | |
| 4. 20 | 2,3,4,5,6-Cl$_5$ | | |
| 4. 21 | 2-Br | | |
| 4. 22 | 3-Br | | |
| 4. 23 | 4-Br | | |
| 4. 24 | 2,4-Br$_2$ | | |
| 4. 25 | 2,5-Br$_2$ | | |
| 4. 26 | 2,6-Br$_2$ | | |
| 4. 27 | 2,4,6-Br$_3$ | | |
| 4. 28 | 2,3,4,5,6-Br$_5$ | | |
| 4. 29 | 2-I | | |
| 4. 30 | 3-I | | |
| 4. 31 | 4-I | | |
| 4. 32 | 2,4-I$_2$ | | |
| 4. 33 | 2-Cl, 3-F | | |
| 4. 34 | 2-Cl, 4-F | | |
| 4. 35 | 2-Cl, 5-F | | |
| 4. 36 | 2-Cl, 6-F | | |
| 4. 37 | 2-Cl, 3-Br | | |
| 4. 38 | 2-Cl, 4-Br | | |

TABLE 4-continued (III)

| No. | $X_m$ | mp (°C.) | IR(cm$^{-1}$) |
|---|---|---|---|
| 4. 39 | 2-Cl, 5-Br | | |
| 4. 40 | 2-Cl, 6-Br | | |
| 4. 41 | 2-Br, 3-Cl | | |
| 4. 42 | 2-Br, 4-Cl | | |
| 4. 43 | 2-Br, 3-F | | |
| 4. 44 | 2-Br, 4-F | | |
| 4. 45 | 2-Br, 4-F | | |
| 4. 46 | 2-Br, 5-F | | |
| 4. 47 | 2-Br, 6-F | | |
| 4. 48 | 2-F, 3-Cl | | |
| 4. 49 | 2-F, 4-Cl | | |
| 4. 50 | 2-F, 5-Cl | | |
| 4. 51 | 3-Cl, 4-F | | |
| 4. 52 | 3-Cl, 5-F | | |
| 4. 53 | 3-Cl, 4-Br | | |
| 4. 54 | 3-Cl, 5-Br | | |
| 4. 55 | 3-F, 4-Cl | | |
| 4. 56 | 3-F, 4-Br | | |
| 4. 57 | 3-Br, 4-Cl | | |
| 4. 58 | 3-Br, 4-F | | |
| 4. 59 | 2,6-Cl$_2$, 4-Br | | |
| 4. 60 | 3-CH$_3$ | | |
| 4. 61 | 2,3-(CH$_3$)$_2$ | | |
| 4. 62 | 2,4-(CH$_3$)$_2$ | oil | 3460, 2915, 1739, 1503, 1254, 1221 |
| 4. 63 | 2,5-(CH$_3$)$_2$ | | |
| 4. 64 | 2,6-(CH$_3$)$_2$ | | |
| 4. 65 | 3,4-(CH$_3$)$_2$ | | |
| 4. 66 | 3,5-(CH$_3$)$_2$ | | |
| 4. 67 | 2,3,4-(CH$_3$)$_3$ | | |
| 4. 68 | 2,3,5-(CH$_3$)$_3$ | | |
| 4. 69 | 2,3,6-(CH$_3$)$_3$ | | |
| 4. 70 | 2,4,5-(CH$_3$)$_3$ | | |
| 4. 71 | 2,4,6-(CH$_3$)$_3$ | | |
| 4. 72 | 3,4,5-(CH$_3$)$_3$ | | |
| 4. 73 | 2,3,4,6-(CH$_3$)$_4$ | | |
| 4. 74 | 2,3,5,6-(CH$_3$)$_4$ | | |
| 4. 75 | 2,3,4,5,6-(CH$_3$)$_5$ | | |
| 4. 76 | 2-C$_2$H$_5$ | | |
| 4. 77 | 3-C$_2$H$_5$ | | |
| 4. 78 | 4-C$_2$H$_5$ | | |
| 4. 79 | 2,4-(C$_2$H$_5$)$_2$ | | |
| 4. 80 | 2,6-(C$_2$H$_5$)$_2$ | | |
| 4. 81 | 3,5-(C$_2$H$_5$)$_2$ | | |
| 4. 82 | 2,4,6-(C$_2$H$_5$)$_3$ | | |
| 4. 83 | 2-n-C$_3$H$_7$ | | |
| 4. 84 | 3-n-C$_3$H$_7$ | | |
| 4. 85 | 4-n-C$_3$H$_7$ | | |
| 4. 86 | 2-i-C$_3$H$_7$ | | |
| 4. 87 | 3-i-C$_3$H$_7$ | | |
| 4. 88 | 4-i-C$_3$H$_7$ | | |
| 4. 89 | 2,4-(i-C$_3$H$_7$)$_2$ | | |
| 4. 90 | 2,6-(i-C$_3$H$_7$)$_2$ | | |
| 4. 91 | 3,5-(i-C$_3$H$_7$)$_2$ | | |
| 4. 92 | 2,4,6-(i-C$_3$H$_7$)$_3$ | | |
| 4. 93 | 2-s-C$_4$H$_9$ | | |
| 4. 94 | 3-s-C$_4$H$_9$ | | |
| 4. 95 | 4-s-C$_4$H$_9$ | | |
| 4. 96 | 2-t-C$_4$H$_9$ | | |
| 4. 97 | 3-t-C$_4$H$_9$ | | |
| 4. 98 | 2,3-(t-C$_4$H$_9$)$_2$ | | |
| 4. 99 | 2,4-(t-C$_4$H$_9$)$_2$ | | |
| 4. 100 | 2,5-(t-C$_4$H$_9$)$_2$ | | |
| 4. 101 | 2,6-(t-C$_4$H$_9$)$_2$ | | |
| 4. 102 | 3,5-(t-C$_4$H$_9$)$_2$ | | |
| 4. 103 | 2,4,6-(t-C$_4$H$_9$)$_3$ | | |
| 4. 104 | 4-n-C$_9$H$_{19}$ | | |
| 4. 105 | 4-n-C$_{12}$H$_{25}$ | | |
| 4. 106 | 3-n-C$_{15}$H$_{31}$ | | |
| 4. 107 | 4-(1,1,3,3-tetramethylbutyl) | | |
| 4. 108 | 4-(2,3,3-trimethylpropyl) | | |
| 4. 109 | 2-t-C$_4$H$_9$, 4-CH$_3$ | | |
| 4. 110 | 2-t-C$_4$H$_9$, 5-CH$_3$ | | |
| 4. 111 | 2,6-(t-C$_4$H$_9$)$_2$, 4-CH$_3$ | | |
| 4. 112 | 2-CH$_3$, 4-t-C$_4$H$_9$ | | |
| 4. 113 | 2-CH$_3$, 6-t-C$_4$H$_9$ | | |
| 4. 114 | 2-CH$_3$, 4-i-C$_3$H$_7$ | | |
| 4. 115 | 2-CH$_3$, 5-i-C$_3$H$_7$ | | |
| 4. 116 | 3-CH$_3$, 4-i-C$_3$H$_7$ | | |
| 4. 117 | 2-i-C$_3$H$_7$, 5-CH$_3$ | | |
| 4. 118 | 2,4-(t-C$_4$H$_9$)$_2$, 6-i-C$_3$H$_7$ | | |
| 4. 119 | 2-C$_3$H$_5$ (= allyl) | | |
| 4. 120 | 3-C$_3$H$_5$ | | |
| 4. 121 | 4-C$_3$H$_5$ | | |
| 4. 122 | 2-C$_3$H$_5$, 6-CH$_3$ | | |
| 4. 123 | 2-cyclo-C$_6$H$_{11}$ | | |
| 4. 124 | 3-cyclo-C$_6$H$_{11}$ | | |
| 4. 125 | 4-cyclo-C$_6$H$_{11}$ | | |
| 4. 126 | 2,4-(cyclo-C$_6$H$_{11}$)$_2$, 6-CH$_3$ | | |
| 4. 127 | 2-CH$_3$, 4-cyclo-C$_6$H$_{11}$ | | |
| 4. 128 | 2-CH$_2$C$_6$H$_5$ | | |
| 4. 129 | 3-CH$_2$C$_6$H$_5$ | | |
| 4. 130 | 4-CH$_2$C$_6$H$_5$ | | |
| 4. 131 | 2-CH$_2$C$_6$H$_5$, 4-CH$_3$ | | |
| 4. 132 | 2-CH$_3$, 4-CH$_2$C$_6$H$_5$ | | |
| 4. 133 | 2-C$_6$H$_5$ | | |
| 4. 134 | 3-C$_6$H$_5$ | | |
| 4. 135 | 4-C$_6$H$_5$ | | |
| 4. 136 | 4-(2-i-C$_3$H$_7$—C$_6$H$_4$) | | |
| 4. 137 | 4-C$_6$H$_5$, 2,6-(CH$_3$)$_2$ | | |
| 4. 138 | 2-Cl, 4-C$_6$H$_5$ | | |
| 4. 139 | 2-Br, 4-C$_6$H$_5$ | | |
| 4. 140 | 2-C$_6$H$_5$, 4-Cl | | |
| 4. 141 | 2-C$_6$H$_5$, 4-Br | | |
| 4. 142 | 2-CH$_2$C$_6$H$_5$, 4-Cl | | |
| 4. 143 | 2-CH$_2$C$_6$H$_5$, 4-Br | | |
| 4. 144 | 2-Cl, 4-CH$_2$C$_6$H$_5$ | | |
| 4. 145 | 2-Br, 4-CH$_2$C$_6$H$_5$ | | |
| 4. 146 | 2-cyclo-C$_6$H$_{11}$, 4-Cl | | |
| 4. 147 | 2-cyclo-C$_6$H$_{11}$, 4-Br | | |
| 4. 148 | 2-Cl, 4-cyclo-C$_6$H$_{11}$ | | |
| 4. 149 | 2-Br, 4-cyclo-C$_6$H$_{11}$ | | |
| 4. 150 | 3-OCH$_3$ | | |
| 4. 151 | 2,4-(OCH$_3$)$_2$ | | |
| 4. 152 | 2-CF$_3$ | | |
| 4. 153 | 3-CF$_3$ | | |
| 4. 154 | 4-CF$_3$ | | |
| 4. 155 | 2-OCF$_3$ | | |
| 4. 156 | 3-OCF$_3$ | | |
| 4. 157 | 4-OCF$_3$ | | |
| 4. 158 | 3-OCH$_2$CHF$_2$ | | |
| 4. 159 | 2-NO$_2$ | | |
| 4. 160 | 3-NO$_2$ | | |
| 4. 161 | 2-CN | | |
| 4. 162 | 3-CN | | |
| 4. 163 | 4-CN | | |
| 4. 164 | 2-CH$_3$, 3-Cl | | |
| 4. 165 | 2-CH$_3$, 5-Cl | | |
| 4. 166 | 2-CH$_3$, 6-Cl | | |
| 4. 167 | 2-CH$_3$, 3-F | | |
| 4. 168 | 2-CH$_3$, 4-F | | |
| 4. 169 | 2-CH$_3$, 5-F | | |
| 4. 170 | 2-CH$_3$, 6-F | | |
| 4. 171 | 2-CH$_3$, 3-Br | | |
| 4. 172 | 2-CH$_3$, 4-Br | | |
| 4. 173 | 2-CH$_3$, 5-Br | | |
| 4. 174 | 2-CH$_3$, 6-Br | | |
| 4. 175 | 2-Cl, 3-CH$_3$ | | |
| 4. 176 | 2-Cl, 4-CH$_3$ | | |
| 4. 177 | 2-Cl, 5-CH$_3$ | | |
| 4. 178 | 2-F, 3-CH$_3$ | | |
| 4. 179 | 2-F, 4-CH$_3$ | | |
| 4. 180 | 2-F, 5-CH$_3$ | | |

TABLE 4-continued

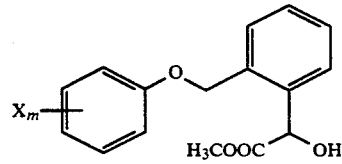
(III)

| No. | $X_m$ | mp (°C.) | IR(cm$^{-1}$) |
|---|---|---|---|
| 4. 181 | 2-Br, 3-CH$_3$ | | |
| 4. 182 | 2-Br, 4-CH$_3$ | | |
| 4. 183 | 3-CH$_3$, 4-Cl | | |
| 4. 184 | 3-CH$_3$, 5-Cl | | |
| 4. 185 | 2-Br, 5-CH$_3$ | | |
| 4. 186 | 3-CH$_3$, 4-F | | |
| 4. 187 | 3-CH$_3$, 5-F | | |
| 4. 188 | 3-CH$_3$, 4-Br | | |
| 4. 189 | 3-CH$_3$, 5-Br | | |
| 4. 190 | 3-F, 4-CH$_3$ | | |
| 4. 191 | 3-Cl, 4-CH$_3$ | | |
| 4. 192 | 3-Br, 4-CH$_3$ | | |
| 4. 193 | 2-Cl, 4,5-(CH$_3$)$_2$ | | |
| 4. 194 | 2-Br, 4,5-(CH$_3$)$_2$ | | |
| 4. 195 | 2-Cl, 3,5-(CH$_3$)$_2$ | | |
| 4. 196 | 2-Br, 3,5-(CH$_3$)$_2$ | | |
| 4. 197 | 2,6-Cl$_2$, 4-CH$_3$ | | |
| 4. 198 | 2,6-F$_2$, 4-CH$_3$ | | |
| 4. 199 | 2,6-Br$_2$, 4-CH$_3$ | | |
| 4. 200 | 2,4-Cl$_2$, 6-CH$_3$ | | |
| 4. 201 | 2,4-F$_2$, 6-CH$_3$ | | |
| 4. 202 | 2,4-Br$_2$, 6-CH$_3$ | | |
| 4. 203 | 2,6-(CH$_3$)$_2$, 4-F | | |
| 4. 204 | 2,6-(CH$_3$)$_2$, 4-Cl | | |
| 4. 205 | 2,6-(CH$_3$)$_2$, 4-Br | | |
| 4. 206 | 3,5-(CH$_3$)$_2$, 4-F | | |
| 4. 207 | 3,5-(CH$_3$)$_2$, 4-Cl | | |
| 4. 208 | 3,5-(CH$_3$)$_2$, 4-Br | | |
| 4. 209 | 2,3,6-(CH$_3$)$_3$, 4-F | | |
| 4. 210 | 2,3,6-(CH$_3$)$_3$, 4-Cl | | |
| 4. 211 | 2,3,6-(CH$_3$)$_3$, 4-Br | | |
| 4. 212 | 2,4-(CH$_3$)$_2$, 6-F | | |
| 4. 213 | 2,4-(CH$_3$)$_2$, 6-Cl | | |
| 4. 214 | 2,4-(CH$_3$)$_2$, 6-Br | | |
| 4. 215 | 2-i-C$_3$H$_7$, 4-Cl, 5-CH$_3$ | | |
| 4. 216 | 2-Cl, 4-NO$_2$ | | |
| 4. 217 | 2-NO$_2$, 4-Cl | | |
| 4. 218 | 2-OCH$_3$, 5-NO$_2$ | | |
| 4. 219 | 2,4-Cl$_2$, 5-NO$_2$ | | |
| 4. 220 | 2,4-Cl$_2$, 6-NO$_2$ | | |
| 4. 221 | 2,6-Cl$_2$, 4-NO$_2$ | | |
| 4. 222 | 2,6-Br$_2$, 4-NO$_2$ | | |
| 4. 223 | 2,6-I$_2$, 4-NO$_2$ | | |
| 4. 224 | 2-CH$_3$, 5-i-C$_3$H$_7$, 4-Cl | | |
| 4. 225 | 2-C$_6$H$_5$O | | |
| 4. 226 | 3-C$_6$H$_5$O | | |
| 4. 227 | 4-C$_6$H$_5$O | | |
| 4. 228 | 3-t-C$_4$H$_9$O | | |
| 4. 229 | 4-t-C$_4$H$_9$O | | |
| 4. 230 | *1) | | |
| 4. 231 | *2) | | |

*1)
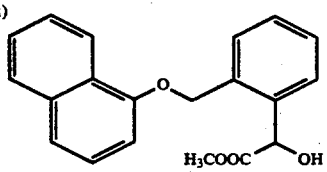

*2)
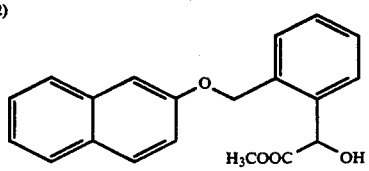

TABLE 5

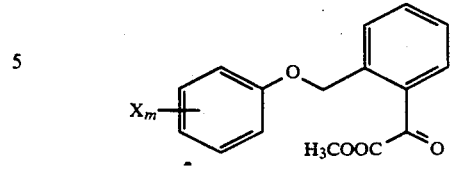
(II)

| No. | $X_m$ | mp (°C.) | IR(cm$^{-1}$) |
|---|---|---|---|
| 5. 1 | 3-F | | |
| 5. 2 | 4-F | | |
| 5. 3 | 2,4-F$_2$ | | |
| 5. 4 | 2,4,6-F$_3$ | | |
| 5. 5 | 2,3,4,5,6-F$_5$ | | |
| 5. 6 | 2,3-F$_2$ | | |
| 5. 7 | 2,3-Cl$_2$ | | |
| 5. 8 | 2,5-Cl$_2$ | | |
| 5. 9 | 2,6-Cl$_2$ | | |
| 5. 10 | 3,4-Cl$_2$ | | |
| 5. 11 | 3,5-Cl$_2$ | | |
| 5. 12 | 2,3,4-Cl$_3$ | | |
| 5. 13 | 2,3,5-Cl$_3$ | | |
| 5. 14 | 2,3,6-Cl$_3$ | | |
| 5. 15 | 2,4,5-Cl$_3$ | | |
| 5. 16 | 2,4,6-Cl$_3$ | | |
| 5. 17 | 3,4,5-Cl$_3$ | | |
| 5. 18 | 2,3,4,6-Cl$_4$ | | |
| 5. 19 | 2,3,5,6-Cl$_4$ | | |
| 5. 20 | 2,3,4,5,6-Cl$_5$ | | |
| 5. 21 | 2-Br | | |
| 5. 22 | 3-Br | | |
| 5. 23 | 4-Br | | |
| 5. 24 | 2,4-Br$_2$ | | |
| 5. 25 | 2,5-Br$_2$ | | |
| 5. 26 | 2,6-Br$_2$ | | |
| 5. 27 | 2,4,6-Br$_3$ | | |
| 5. 28 | 2,3,4,5,6-Br$_5$ | | |
| 5. 29 | 2-I | | |
| 5. 30 | 3-I | | |
| 5. 31 | 4-I | | |
| 5. 32 | 2,4-I$_2$ | | |
| 5. 33 | 2-Cl, 3-F | | |
| 5. 34 | 2-Cl, 4-F | | |
| 5. 35 | 2-Cl, 5-F | | |
| 5. 36 | 2-Cl, 6-F | | |
| 5. 37 | 2-Cl, 3-Br | | |
| 5. 38 | 2-Cl, 4-Br | | |
| 5. 39 | 2-Cl, 5-Br | | |
| 5. 40 | 2-Cl, 6-Br | | |
| 5. 41 | 2-Br, 3-Cl | | |
| 5. 42 | 2-Br, 4-Cl | | |
| 5. 43 | 2-Br, 3-F | | |
| 5. 45 | 2-Br, 4-F | | |
| 5. 46 | 2-Br, 5-F | | |
| 5. 47 | 2-Br, 6-F | | |
| 5. 48 | 2-F, 3-Cl | | |
| 5. 49 | 2-F, 4-Cl | | |
| 5. 50 | 2-F, 5-Cl | | |
| 5. 51 | 3-Cl, 4-F | | |
| 5. 52 | 3-Cl, 5-F | | |
| 5. 53 | 3-Cl, 4-Br | | |
| 5. 54 | 3-Cl, 5-Br | | |
| 5. 55 | 3-F, 4-Cl | | |
| 5. 56 | 3-F, 4-Br | | |
| 5. 57 | 3-Br, 4-Cl | | |
| 5. 58 | 3-Br, 4-F | | |
| 5. 59 | 2,6-Cl$_2$, 4-Br | | |
| 5. 60 | 3-CH$_3$ | | 1732, 1699, 1601, 1258, 1204, 1156, 760 |
| 5. 61 | 2,3-(CH$_3$)$_2$ | | |
| 5. 62 | 2,4-(CH$_3$)$_2$ | | 1734, 1678, 1505, 1258, 1207, 1137, 1007, 796 |
| 5. 63 | 2,5-(CH$_3$)$_2$ | | |
| 5. 64 | 2,6-(CH$_3$)$_2$ | | |
| 5. 65 | 3,4-(CH$_3$)$_2$ | | |
| 5. 66 | 3,5-(CH$_3$)$_2$ | | |
| 5. 67 | 2,3,4-(CH$_3$)$_3$ | | |
| 5. 68 | 2,3,5-(CH$_3$)$_3$ | | |
| 5. 69 | 2,3,6-(CH$_3$)$_3$ | | |
| 5. 70 | 2,4,5-(CH$_3$)$_3$ | | |

TABLE 5-continued

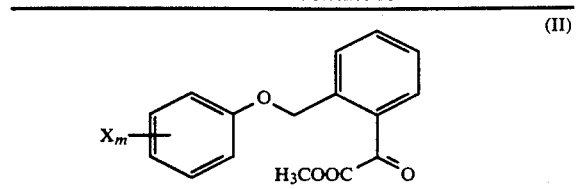
(II)

| No. | $X_m$ | mp (°C.) | IR(cm$^{-1}$) |
|---|---|---|---|
| 5. 71 | 2,4,6-(CH$_3$)$_3$ | | |
| 5. 72 | 3,4,5-(CH$_3$)$_3$ | | |
| 5. 73 | 2,3,4,6-(CH$_3$)$_4$ | | |
| 5. 74 | 2,3,5,6-(CH$_3$)$_4$ | | |
| 5. 75 | 2,3,4,5,6-(CH$_3$)$_5$ | | |
| 5. 76 | 2-C$_2$H$_5$ | | |
| 5. 77 | 3-C$_2$H$_5$ | | |
| 5. 78 | 4-C$_2$H$_5$ | | |
| 5. 79 | 2,4-(C$_2$H$_5$)$_2$ | | |
| 5. 80 | 2,6-(C$_2$H$_5$)$_2$ | | |
| 5. 81 | 3,5-(C$_2$H$_5$)$_2$ | | |
| 5. 82 | 2,4,6-(C$_2$H$_5$)$_3$ | | |
| 5. 83 | 2-n-C$_3$H$_7$ | | |
| 5. 84 | 3-n-C$_3$H$_7$ | | |
| 5. 85 | 4-n-C$_3$H$_7$ | | |
| 5. 86 | 2-i-C$_3$H$_7$ | | |
| 5. 87 | 3-i-C$_3$H$_7$ | | |
| 5. 88 | 4-i-C$_3$H$_7$ | | |
| 5. 89 | 2,4-(i-C$_3$H$_7$)$_2$ | | |
| 5. 90 | 2,6-(i-C$_3$H$_7$)$_2$ | | |
| 5. 91 | 3,5-(i-C$_3$H$_7$)$_2$ | | |
| 5. 92 | 2,4,6-(i-C$_3$H$_7$)$_3$ | | |
| 5. 93 | 2-s-C$_4$H$_9$ | | |
| 5. 94 | 3-s-C$_4$H$_9$ | | |
| 5. 95 | 4-s-C$_4$H$_9$ | | |
| 5. 96 | 2-t-C$_4$H$_9$ | | |
| 5. 97 | 3-t-C$_4$H$_9$ | | |
| 5. 98 | 2,3-(t-C$_4$H$_9$)$_2$ | | |
| 5. 99 | 2,4-(t-C$_4$H$_9$)$_2$ | | |
| 5. 100 | 2,5-(t-C$_4$H$_9$)$_2$ | | |
| 5. 101 | 2,6-(t-C$_4$H$_9$)$_2$ | | |
| 5. 102 | 3,5-(t-C$_4$H$_9$)$_2$ | | |
| 5. 103 | 2,4,6-(t-C$_4$H$_9$)$_3$ | | |
| 5. 104 | 4-n-C$_9$H$_{19}$ | | |
| 5. 105 | 4-n-C$_{12}$H$_{25}$ | | |
| 5. 106 | 3-n-C$_{15}$H$_{31}$ | | |
| 5. 107 | 4-(1,1,3,3-tetramethylbutyl) | | |
| 5. 108 | 4-(2,3,3-trimethylpropyl) | | |
| 5. 109 | 2-t-C$_4$H$_9$, 4-CH$_3$ | | |
| 5. 110 | 2-t-C$_4$H$_9$, 5-CH$_3$ | | |
| 5. 111 | 2,6-(t-C$_4$H$_9$)$_2$, 4-CH$_3$ | | |
| 5. 112 | 2-CH$_3$, 4-t-C$_4$H$_9$ | | |
| 5. 113 | 2-CH$_3$, 6-t-C$_4$H$_9$ | | |
| 5. 114 | 2-CH$_3$, 4-i-C$_3$H$_7$ | | |
| 5. 115 | 2-CH$_3$, 5-i-C$_3$H$_7$ | | |
| 5. 116 | 3-CH$_3$, 4-i-C$_3$H$_7$ | | |
| 5. 117 | 2-i-C$_3$H$_7$, 5-CH$_3$ | | |
| 5. 118 | 2,4-(t-C$_4$H$_9$)$_2$, 6-i-C$_3$H$_7$ | | |
| 5. 119 | 2-C$_3$H$_5$ (= allyl) | | |
| 5. 120 | 3-C$_3$H$_5$ | | |
| 5. 121 | 4-C$_3$H$_5$ | | |
| 5. 122 | 2-C$_3$H$_5$, 6-CH$_3$ | | |
| 5. 123 | 2-cyclo-C$_6$H$_{11}$ | | |
| 5. 124 | 3-cyclo-C$_6$H$_{11}$ | | |
| 5. 125 | 4-cyclo-C$_6$H$_{11}$ | | |
| 5. 126 | 2,4-(cyclo-C$_6$H$_{11}$)$_2$, 6-CH$_3$ | | |
| 5. 127 | 2-CH$_3$, 4-cyclo-C$_6$H$_{11}$ | | |
| 5. 128 | 2-CH$_2$C$_6$H$_5$ | | |
| 5. 129 | 3-CH$_2$C$_6$H$_5$ | | |
| 5. 130 | 4-CH$_2$C$_6$H$_5$ | | |
| 5. 131 | 2-CH$_2$C$_6$H$_5$, 4-CH$_3$ | | |
| 5. 132 | 2-CH$_3$, 4-CH$_2$C$_6$H$_5$ | | |
| 5. 133 | 2-C$_6$H$_5$ | | |
| 5. 134 | 3-C$_6$H$_5$ | | |
| 5. 135 | 4-C$_6$H$_5$ | | |
| 5. 136 | 4-(2-i-C$_3$H$_7$—C$_6$H$_4$) | | |
| 5. 137 | 4-C$_6$H$_5$, 2,6-(CH$_3$)$_2$ | | |
| 5. 138 | 2-Cl, 4-C$_6$H$_5$ | | |
| 5. 139 | 2-Br, 4-C$_6$H$_5$ | | |
| 5. 140 | 2-C$_6$H$_5$, 4-Cl | | |
| 5. 141 | 2-C$_6$H$_5$, 4-Br | | |

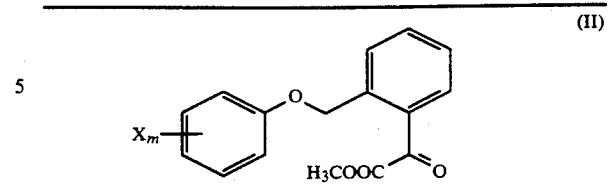
(II)

| No. | $X_m$ | mp (°C.) | IR(cm$^{-1}$) |
|---|---|---|---|
| 5. 142 | 2-CH$_2$C$_6$H$_5$, 4-Cl | | |
| 5. 143 | 2-CH$_2$C$_6$H$_5$, 4-Br | | |
| 5. 144 | 2-Cl, 4-CH$_2$C$_6$H$_5$ | | |
| 5. 145 | 2-Br, 4-CH$_2$C$_6$H$_5$ | | |
| 5. 146 | 2-cyclo-C$_6$H$_{11}$, 4-Cl | | |
| 5. 147 | 2-cyclo-C$_6$H$_{11}$, 4-Br | | |
| 5. 148 | 2-Cl, 4-cyclo-C$_6$H$_{11}$ | | |
| 5. 149 | 2-Br, 4-cyclo-C$_6$H$_{11}$ | | |
| 5. 150 | 3-OCH$_3$ | oil | 1742, 1670, 1597, 1276, 1011, 755 |
| 5. 151 | 2,4-(OCH$_3$)$_2$ | | |
| 5. 152 | 2-CF$_3$ | | |
| 5. 153 | 3-CF$_3$ | | |
| 5. 154 | 4-CF$_3$ | | |
| 5. 155 | 2-OCF$_3$ | | |
| 5. 156 | 3-OCF$_3$ | | |
| 5. 157 | 4-OCF$_3$ | | |
| 5. 158 | OCH$_2$CHF$_2$ | | |
| 5. 159 | 2-NO$_2$ | | |
| 5. 160 | 3-NO$_2$ | | |
| 5. 161 | 2-CN | | |
| 5. 162 | 3-CN | | |
| 5. 163 | 4-CN | | |
| 5. 164 | 2-CH$_3$, 3-Cl | | |
| 5. 165 | 2-CH$_3$, 5-Cl | | |
| 5. 166 | 2-CH$_3$, 6-Cl | | |
| 5. 167 | 2-CH$_3$, 3-F | | |
| 5. 168 | 2-CH$_3$, 4-F | | |
| 5. 169 | 2-CH$_3$, 5-F | | |
| 5. 170 | 2-CH$_3$, 6-F | | |
| 5. 171 | 2-CH$_3$, 3-Br | | |
| 5. 172 | 2-CH$_3$, 4-Br | | |
| 5. 173 | 2-CH$_3$, 5-Br | | |
| 5. 174 | 2-CH$_3$, 6-Br | | |
| 5. 175 | 2-Cl, 3-CH$_3$ | | |
| 5. 176 | 2-Cl, 4-CH$_3$ | | |
| 5. 177 | 2-Cl, 5-CH$_3$ | | |
| 5. 178 | 2-F, 3-CH$_3$ | | |
| 5. 179 | 2-F, 4-CH$_3$ | | |
| 5. 180 | 2-F, 5-CH$_3$ | | |
| 5. 181 | 2-Br, 3-CH$_3$ | | |
| 5. 182 | 2-Br, 4-CH$_3$ | | |
| 5. 183 | 3-CH$_3$, 4-Cl | | |
| 5. 184 | 3-CH$_3$, 5-Cl | | |
| 5. 185 | 2-Br, 5-CH$_3$ | | |
| 5. 186 | 3-CH$_3$, 4-F | | |
| 5. 187 | 3-CH$_3$, 5-F | | |
| 5. 188 | 3-CH$_3$, 4-Br | | |
| 5. 189 | 3-CH$_3$, 5-Br | | |
| 5. 190 | 3-F, 4-CH$_3$ | | |
| 5. 191 | 3-Cl, 4-CH$_3$ | | |
| 5. 192 | 3-Br, 4-CH$_3$ | | |
| 5. 193 | 2-Cl, 4,5-(CH$_3$)$_2$ | | |
| 5. 194 | 2-Br, 4,5-(CH$_3$)$_2$ | | |
| 5. 195 | 2-Cl, 3,5-(CH$_3$)$_2$ | | |
| 5. 196 | 2-Br, 3,5-(CH$_3$)$_2$ | | |
| 5. 197 | 2,6-Cl$_2$, 4-CH$_3$ | | |
| 5. 198 | 2,6-F$_2$, 4-CH$_3$ | | |
| 5. 199 | 2,6-Br$_2$, 4-CH$_3$ | | |
| 5. 200 | 2,4-Cl$_2$, 6-CH$_3$ | | |
| 5. 201 | 2,4-F$_2$, 6-CH$_3$ | | |
| 5. 202 | 2,4-Br$_2$, 6-CH$_3$ | | |
| 5. 203 | 2,6-(CH$_3$)$_2$, 4-F | | |
| 5. 204 | 2,6-(CH$_3$)$_2$, 4-Cl | | |
| 5. 205 | 2,6-(CH$_3$)$_2$, 4-Br | | |
| 5. 206 | 3,5-(CH$_3$)$_2$, 4-F | | |
| 5. 207 | 3,5-(CH$_3$)$_2$, 4-Cl | | |
| 5. 208 | 3,5-(CH$_3$)$_2$, 4-Br | | |
| 5. 209 | 2,3,6-(CH$_3$)$_3$, 4-F | | |
| 5. 210 | 2,3,6-(CH$_3$)$_3$, 4-Cl | | |
| 5. 211 | 2,3,6-(CH$_3$)$_3$, 4-Br | | |

TABLE 5-continued (II)

[structure shown: Xm-substituted phenyl-O-CH2-phenyl-COOCH3]

| No. | Xm | mp (°C.) | IR(cm⁻¹) |
|---|---|---|---|
| 5. 212 | 2,4-(CH₃)₂, 6-F | | |
| 5. 213 | 2,4-(CH₃)₂, 6-Cl | | |
| 5. 214 | 2,4-(CH₃)₂, 6-Br | | |
| 5. 215 | 2-i-C₃H₇, 4-Cl, 5-CH₃ | | |
| 5. 216 | 2-Cl, 4-NO₂ | | |
| 5. 217 | 2-NO₂, 4-Cl | | |
| 5. 218 | 2-OCH₃, 5-NO₂ | | |
| 5. 219 | 2,4-Cl₂, 5-NO₂ | | |
| 5. 220 | 2,4-Cl₂, 6-NO₂ | | |
| 5. 221 | 2,6-Cl₂, 4-NO₂ | | |
| 5. 222 | 2,6-Br₂, 4-NO₂ | | |
| 5. 223 | 2,6-I₂, 4-NO₂ | | |
| 5. 224 | 2-CH₃, 5-i-C₃H₇, 4-Cl | | |
| 5. 225 | 2-C₆H₅O | | |
| 5. 226 | 3-C₆H₅O | | |
| 5. 227 | 4-C₆H₅O | | |
| 5. 228 | 3-t-C₄H₉O | | |
| 5. 229 | 4-t-C₄H₉O | | |
| 5. 230 | *1) | | |
| 5. 231 | *2) | | |

*1)
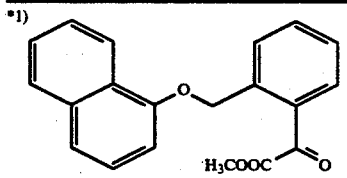

*2)
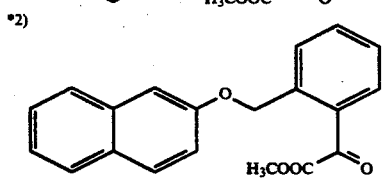

Generally speaking, the novel compounds are extremely effective on a broad spectrum of phytopathogenic fungi, in particular those from the Ascomycetes and Basidiomycetes classes. Some of them have a systemic action and can be sued as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
Plasmopara viticola in grapes,
Alternaria species in vegetables and fruit.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvent and/or carriers, with or without the use of emulsifiers and dispersants; if water is used as solvent, it is also possible to employ other organic solvents as auxiliary solvent. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt% of active ingredient. The application rates are from 0.02 to 3 kg or more of active ingredient per hectare, depending on the type of effect desired. The novel compounds may also be used for protecting materials, for example against Paecilomyces variotii.

When the active ingredients are used for treating seed, amounts of from 0.001 to 50, and preferably from 0.01 to 10, g per kg of seed are usually employed.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1.1 is mixed with 10 parts by weight of N-methyl-α-pyrrolidone. A mixture is obtained which is suitable for application in the form of very fine drops.

II. 20 parts by weight of compound no. 1.2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III 20 parts by weight of compound no. 1.3 is dissolved in a mixture consisting of 40 parts by weight of cyclohexanonone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1.7 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 1.10 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 1.21 is intimately mixed with 97 parts by weight of particulate kaolin. A dust is obtained containing 3% by weight of the active ingredient.

VIII. 30 parts by weight of compound no. 1.34 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1.38 is intimately mixed with 10 parts by weight of the sodium slat of a phenolsulfonic acid-urea-formaldehyde condensate, 2 parts of silica gel and 48 parts of water to give a stable aqueous dispersion. Dilution in water given an aqueous dispersion.

IX. 20 parts by weight of compound no. 1.153 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLES

For comparison purposes, the compound 2-phenoxymethylphenylglyoxylic acid methyl ester-O-methyloxime (A) disclosed in E 253,213 was used.

USE EXAMPLE

Action on *Pyrenophora teres*

Barley seedings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus *Pyrenophora teres*, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

The results show that active ingredients 1.1, 1.2, 1.3, 1.7, 1.10, 1.21, 1.34, 1.38, 1.45, 1.60, 1.61, 1.62, 1.72, 1.97, 1.115, 1.135, 1.138, 1.153 and 1.157, applied as 0.05 wt% spray liquors, had a better fungicidal action (97%) than prior art comparative agent A (55%).

We claim:

1. A compound of the formula

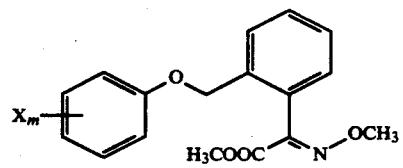

wherein $X_m$ is selected from the group consisting of:
$C_3$–$C_6$-alkenyl;
$C_1$–$C_2$-haloalkoxy;
$C_3$–$C_6$-cycloalkyl;
phenyl;
3-methyl;
2,3-dimethyl;
2,4-dimethyl;
2,5-dimethyl;
2,6-dimethyl;
3,4-dimethyl;
2,3,5-trimethyl;
2,4,5-trimethyl;
3,4,5-trimethyl;
3-t-butyl;
2-methyl-4-t-butyl;
3,5-diethyl;
4n-nonyl;
2-methyl-4-cyclohexyl;
2-benzyl-4-methyl;
2-chloro-4-phenyl;
hexyloxy;
2-methyl-5-isopropyl;
3-methyl-5-isopropyl;
3,4-cyclohexano;
2,3- or 3,4-benzo; and
2-allyl-6-methyl.

2. A fungicidal composition comprising an inert carrier and a fungicidally effective amount of a compound of claim 1.

3. A method for combating fungi, comprising contacting the fungi, or the materials, plants, seed, or soil threatened by fungal attach with a fungicidally effective amount of a compound of claim 1.

4. A compound of claim 1, wherein $X_m$ is 2,4-dimethyl.

5. A compound of claim 1, wherein $X_m$ is 2,3,5-$(CH_3)_3$.

6. A compound of claim 1, wherein $X_m$ is 3-methyl.

7. A compound of claim 1, wherein $X_m$ is 3-t-butyl.

* * * * *